United States Patent
Owczarek et al.

(10) Patent No.: US 11,091,443 B2
(45) Date of Patent: Aug. 17, 2021

(54) FLEXIBLE PIEZOELECTRIC AND FERROELECTRIC HALOIMIDAZOLE CRYSTALS

(71) Applicants: NORTHWESTERN UNIVERSITY, Evanston, IL (US); KING ABDULAZIZ CITY FOR SCIENCE AND TECHNOLOGY (KACST), Riyadh (SA); UCHICAGO ARGONNE, LLC, Chicago, IL (US)

(72) Inventors: Magdalena Owczarek, Chicago, IL (US); Karl A. Hujsak, Evanston, IL (US); Daniel P. Ferris, Evanston, IL (US); Aleksandrs Prokofjevs, Evanston, IL (US); Dravid P. Vinayak, Glenview, IL (US); James Fraser Stoddart, Evanston, IL (US); Daniel Seungbum Hong, Chicago, IL (US)

(73) Assignees: NORTHWESTERN UNIVERSITY, Evanston, IL (US); KING ABDULAZIZ CITY FOR SCIENCE AND TECHNOLOGY (KACST), Riyadh (SA); UCHICAGO ARGONNE, LLC, Chicago, IL (US)

( * ) Notice: Subject to any disclaimer, the term of this patent is extended or adjusted under 35 U.S.C. 154(b) by 273 days.

(21) Appl. No.: 16/093,256

(22) PCT Filed: Apr. 12, 2017

(86) PCT No.: PCT/US2017/027170
§ 371 (c)(1),
(2) Date: Oct. 12, 2018

(87) PCT Pub. No.: WO2017/180721
PCT Pub. Date: Oct. 19, 2017

(65) Prior Publication Data
US 2019/0127331 A1    May 2, 2019

Related U.S. Application Data

(60) Provisional application No. 62/382,994, filed on Sep. 2, 2016, provisional application No. 62/321,290, filed on Apr. 12, 2016.

(51) Int. Cl.
| | | |
|---|---|---|
| C07D 233/68 | (2006.01) | |
| H01L 41/45 | (2013.01) | |
| H01L 41/193 | (2006.01) | |
| C07D 233/56 | (2006.01) | |
| H01L 41/18 | (2006.01) | |

(52) U.S. Cl.
CPC ......... C07D 233/68 (2013.01); C07D 233/56 (2013.01); H01L 41/18 (2013.01); H01L 41/193 (2013.01); H01L 41/45 (2013.01)

(58) Field of Classification Search
CPC ..... C07D 233/68; H01L 41/193; H01L 41/18; H01L 41/45
See application file for complete search history.

(56) References Cited

U.S. PATENT DOCUMENTS

| | | | | |
|---|---|---|---|---|
| 3,409,606 | A | * 11/1968 | Lutz | C07D 233/68 548/343.1 |
| 3,435,050 | A | * 3/1969 | Wasco | C07D 233/68 548/343.1 |
| 3,997,552 | A | 12/1976 | Buchel | |
| 4,185,991 | A | 1/1980 | Sasse | |
| 2011/0000060 | A1 | 1/2011 | Lee | |
| 2013/0334930 | A1 | 12/2013 | Kang | |
| 2015/0200351 | A1 | 7/2015 | Zawada | |
| 2016/0099403 | A1 | 4/2016 | Tanimoto | |

FOREIGN PATENT DOCUMENTS

| | | | |
|---|---|---|---|
| EP | 2141151 | A1 | 1/2010 |
| EP | 2141151 | * | 1/2020 |

OTHER PUBLICATIONS

Andrzejewski. Michal, et al. Halogen and hydrogen bond architectures in switchable chains of di-and trihaloimidazoles Crystal Growth & Design 15.4 (2015): 1658-1665, Feb. 20, 2015.*
Cliff. M D. et al "Synthesis of 4. 4-Biimidazoles", Synthesis 1994.07 (1994): 681-682.*
Serpell, C. J. & et al. "Intermolecular interactions in bromo-, methyl-, and cyanoimidazole derivatives". Cryst. Growth Des. 13. 2866-2871.(2013).*
Andrzejewski, Michal, et al. "Halogen and hydrogen bond architectures in switchable chains of di-and trihaloimidazoles." Crystal Growth & Design 15A (2015): 1658-1665.
Bader, R. F. W., et al. Description of conjugation and hyperconjugation in terms of electron distributions. J. Am. Chem. Soc. 105, 5061-5068, (1983).
Bahnous, M., et al. 25 Convenient multi-gram scale synthesis of polybrominated imidazoles building blocks. Tetrahedron Lett. 47, 1949-1951, (2006).
Choi, H., et al. Quantitative measurement of in-plane cantilever torsion for calibrating lateral piezoresponse force microscopy. Rev. Sci. Instrum. 82, 113706, (2011).
Choi, Y.-Y. et al. Enhancement of Local Piezoresponse in Polymer Ferroelectrics via Nanoscale Control of Microstructure. ACS Nano 9, 1809-1819, (2015).

(Continued)

*Primary Examiner* — C Melissa Koslow
(74) *Attorney, Agent, or Firm* — Quarles & Brady LLP; Tolga Gulmen

(57) ABSTRACT

Provided herein are substituted haloimidazole crystals, the substituted haloimidazole crystal comprising a substituted haloimidazole compound wherein the substituents are selected from the group consisting of hydrogen, an alkyl, and a halogen. The substituted haloimidazole crystals may further comprise second substituted haloimidazole. The substituted haloimidazole crystals may be piezoelectric, ferroelectric, flexible, or any combination thereof. Also provided herein are methods for preparing substituted haloimidazole crystals.

22 Claims, 18 Drawing Sheets

(56) References Cited

OTHER PUBLICATIONS

Desiraju, G. R. et al. Definition of the halogen bond (IUPAC Recommendations 2013). Pure Appl. Chem. 85, 1711-1713, (2013).

Dey, D., et al. Computational study of the formation of short centrosymmetric N—H—S supramolecular synthon and related weak interactions in crystalline 25 1,2,4-triazoles. Cryst. Growth Des. 14, 5881-5896, (2014).

Dickens, B., et al. Hysteresis measurements of remanent polarization and coercive field in polymers. J. Appl. Phys. 72, 4258-4264, (1992).

Dolomanov, O. V., et al. OLEX2: a complete structure solution, refinement and analysis program. J. Appl. Crystallogr. 42, 339-341, (2009).

Dragan, D. Ferroelectric, dielectric and piezoelectric properties of ferroelectric thin films and ceramics. Rep. Prog. Phys. 61, 1267, (1998).

European Patent Office, European Partial Supplementary Search Report for application 17783042.9, dated Sep. 23, 2019.

Fu, D.-W. et al. Diisopropylammonium bromide is a high-temperature molecular ferroelectric crystal. Science 339, 425-428, (2013).

Furukawa, T. Ferroelectric properties of vinylidene fluoride copolymers. Phase Transitions 18, 143-211, (1989).

Ghosh, S., et al. Designing elastic organic crystals: Highly flexible polyhalogenated N-benzylideneanilines. Angew. Chem. Int. Ed. 54, 2674-2678, (2015).

Gilligan, P. J. et al. Synthesis of 6-substituted imidazo[4,5-d]pyridazin-7-ones. Heterocycles 60, 1329-1337, (2003).

Grosse, S. et al. Access to imidazo[1,2-a]imidazolin-2-ones and functionalization through Suzuki-Miyaura cross-coupling reactions. Eur. J. Org. Chem. 2013, 4146-4155, (2013).

Han, S.-T., et al. Towards the development of flexible non-volatile memories. Adv. Mater. 25, 5425-5449, (2013).

Havriliak, S. et al. A complex plane representation of dielectric and mechanical relaxation processes in some polymers. Polymer 8, 161-210, (1967).

Hong, S. et al. Principle of ferroelectric domain imaging using atomic force microscope. J. Appl. Phys. 89, 1377-1386, (2001).

Horiuchi, S. et al. Above-room-temperature ferroelectricity and antiferroelectricity in benzimidazoles. Nat. Commun. 3, 1308, (2012).

International Searching Authority, International Search Report and Written Opinion for application PCT/US2017/027170, dated Sep. 5, 2017.

Koch, U. et al. Characterization of C—H—O hydrogen bonds on the basis of the charge density. J. Phys. Chem. 99, 9747-9754, (1995).

Kochergin P. M. "Study in the imidazole series XVI. Formation of 1-methyl-4,5-dihalo- and 1-methyl-2,4,5-trihaloimidazoles" Abstract only, XP002793851, retrieved from STN Database Accession No. 1965:480619. Database CA Chemical Abstracts Service, Columbus, OH US.

Lutz, A. W. et al. Novel halogenated imidazoles. Chloroimidazoles. J. Heterocycl. Chem. 4, 399-402, (1967).

Mata, I., et al. Relationships between interaction energy, intermolecular distance and electron density properties in hydrogen bonded complexes under external electric fields. Chem. Phys. Lett. 507, 185-189, (2011).

Mukherjee, A. et al. Halogen bonds in some dihalogenated phenols: applications to crystal engineering. IUCrJ 1, 49-60, (2014).

Murata, T., et al. Hydrogen-bonded networks of 2,2'-substituted 4,4'-biimidazoles: New ligands for the assembled metal complexes. Polyhedron 24, 2625-2631, (2005).

Panda, M. K. et al. Spatially resolved analysis of short-range structure perturbations in a plastically bent molecular crystal. Nat. Chem. 7, 65-72, (2015).

Park, M. et al. Three-dimensional ferroelectric domain imaging of epitaxial BiFeO3 thin films using angle-resolved piezoresponse force microscopy. Appl. Phys. Lett. 97, 112907, (2010).

Quan, X., et al. Single-Molecule Piezoelectric Deformation: Rational Design from First-Principles Calculations. The Journal of Physical Chemistry C. 2013, 117 (33), pp. 16783-16790.

Reddy, C. M., et al. Isostructurality, polymorphism and mechanical properties of some hexahalogenated benzenes: The nature of halogen—halogen interactions. Chem. Eur. J. 12, 2222-2234, (2006).

Reddy, C. M., et al. Structure-property correlations in bending and brittle organic crystals. Cryst. Growth Des. 6, 2720-2731, (2006).

Sarma, J. A. R. P. et al. The chloro-substituent as a steering group: A comparative study of non-bonded interactions and hydrogen bonding in crystalline chloro-aromatics. Chem. Phys. Lett. 117, 160-164, (1985).

Sarma, J. A. R. P. et al. The role of Ci—Ci and C—H—O interactions in the crystal engineering of 4-Å short-axis structures. Acc. Chem. Res. 19, 222-228, (1986).

Sheldrick, G. A short history of SHELX. Acta Crystallogr. Sect. A: Found. Crystallogr. 64, 112-122, (2008).

Tagantsev, A. K. et al. The origin of antiferroelectricity in PbZrO3. Nat. Commun. 4, 2229, (2013).

Takamizawa, S. et al. Superelastic organic crystals. Angew. Chem. Int. Ed. 53, 6970-6973, (2014).

Takamizawa, S. et al. Superelastic shape recovery of mechanically twinned 3,5-difluorobenzoic acid crystals. Angew. Chem. Int. Ed. 54, 4815-4817, (2015).

Tayi, A. S. et al. Room-temperature ferroelectricity in supramolecular networks of charge-transfer complexes. Nature 488, 485-489, (2012).

Von Hippel, A. Ferroelectricity, Domain Structure, and Phase Transitions of Barium Titanate. Reviews of Modern Physics 22, 221-237, (1950).

European Patent Office, Extended European Search Report for application 17783042.9. dated Jan. 21, 2020.

* cited by examiner

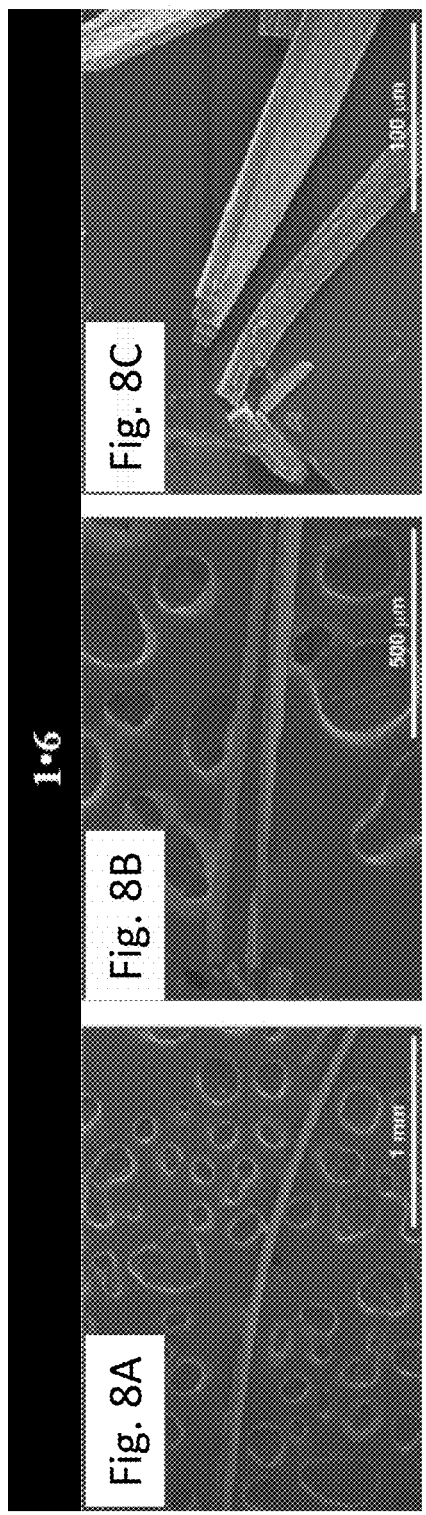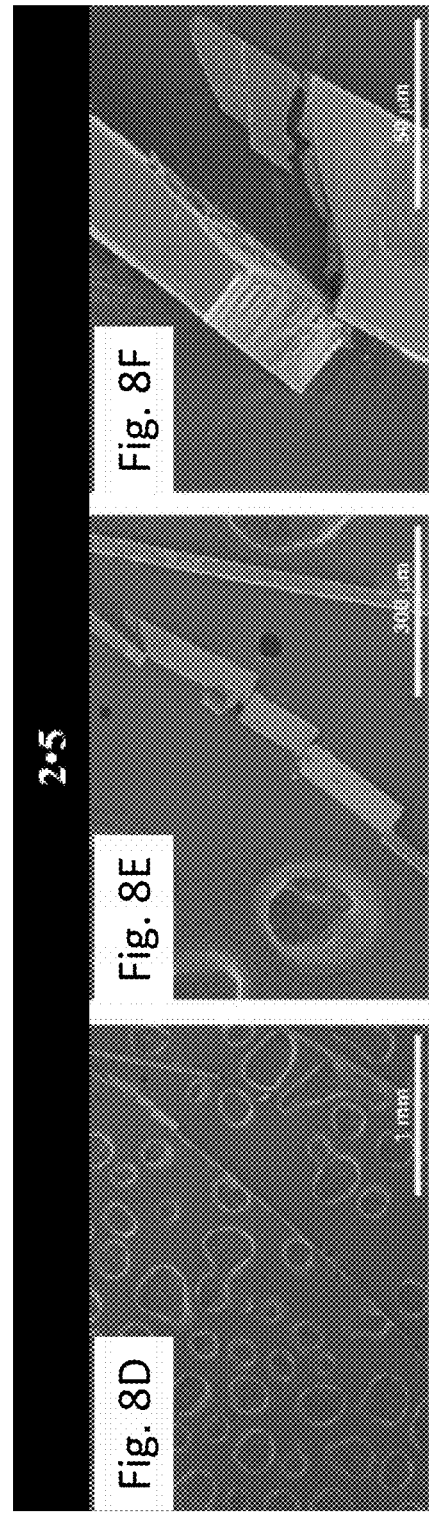

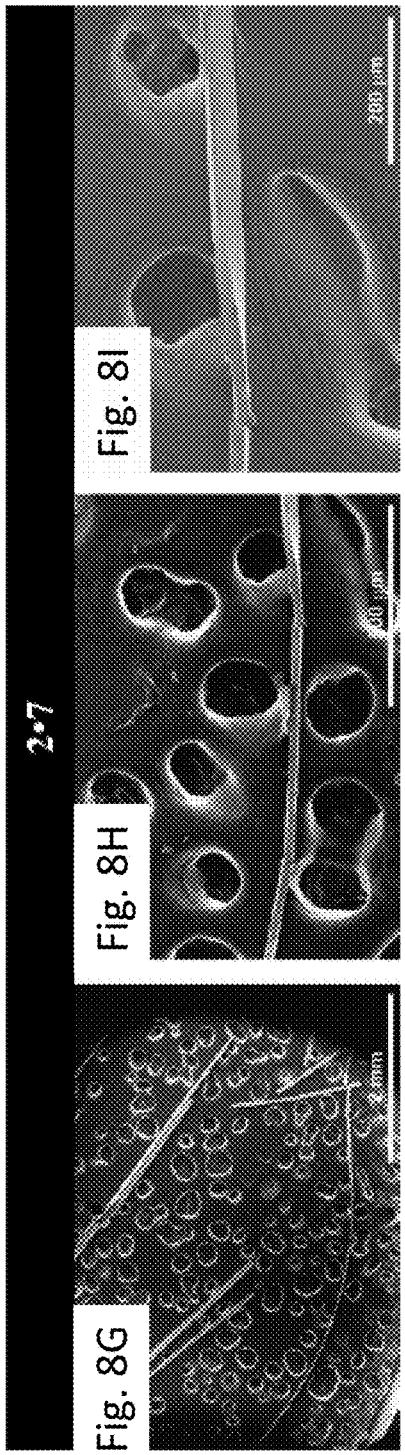
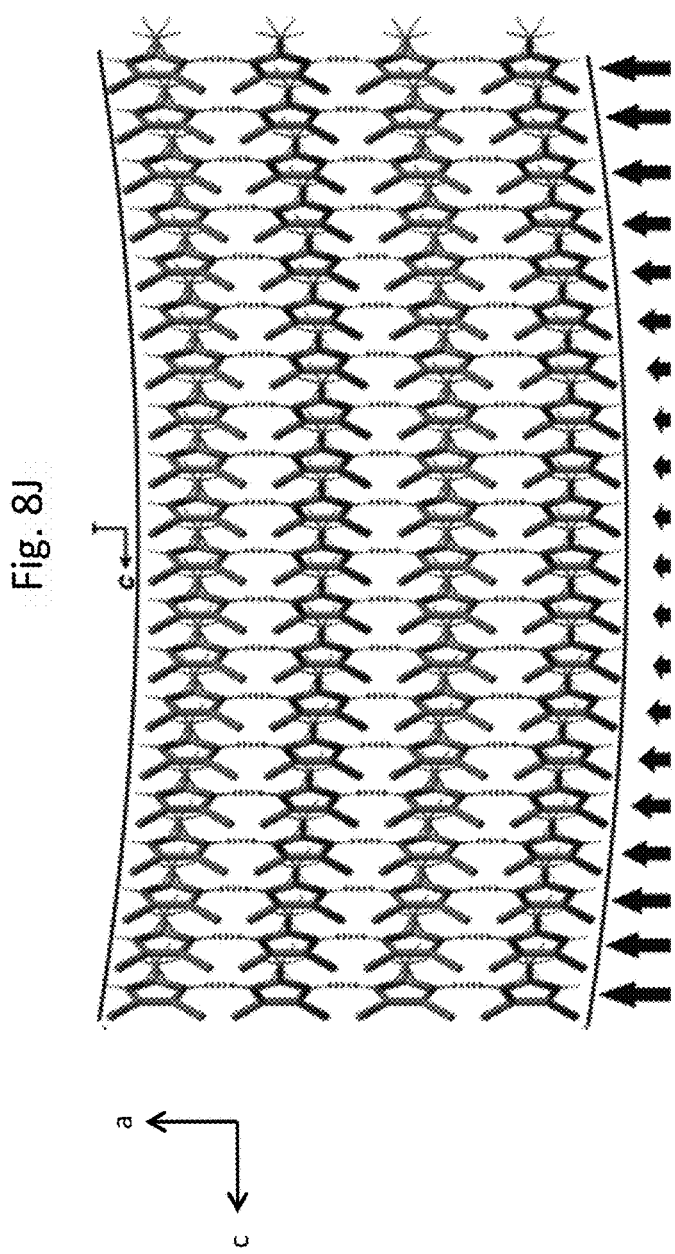

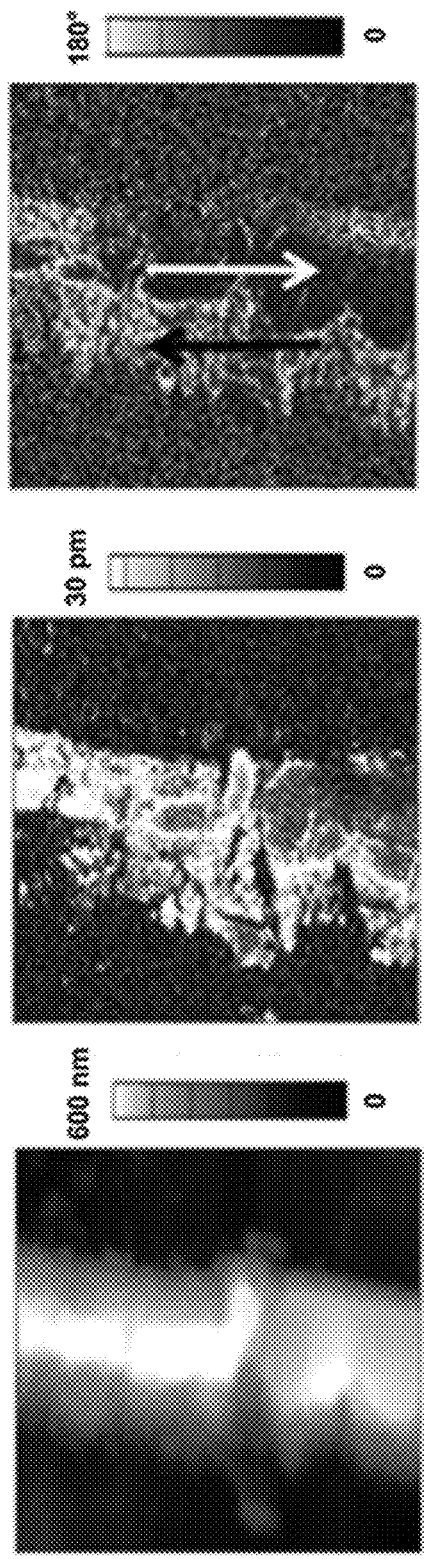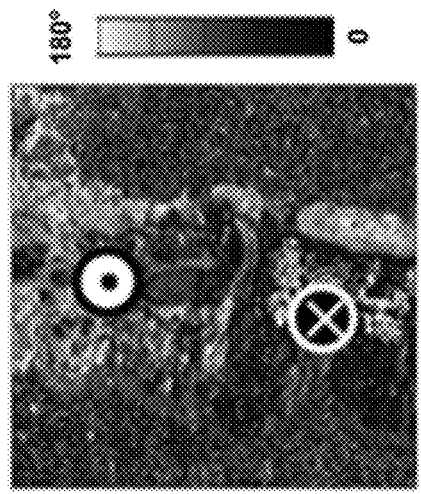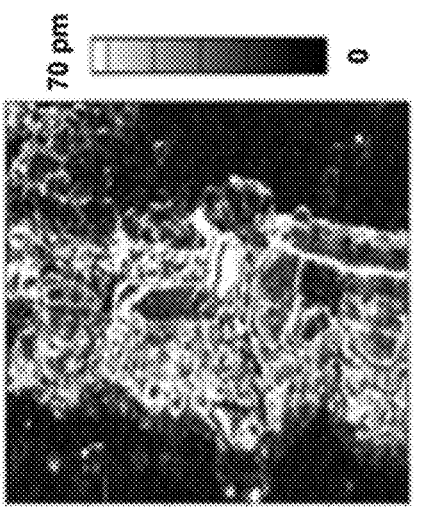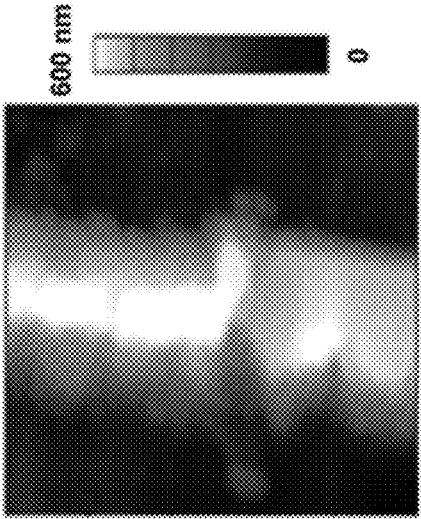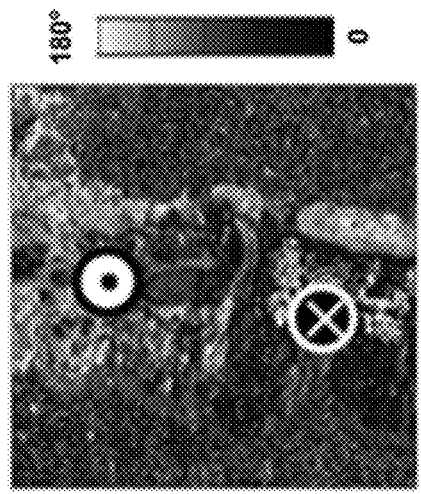

FLEXIBLE PIEZOELECTRIC AND FERROELECTRIC HALOIMIDAZOLE CRYSTALS

CROSS-REFERENCE TO RELATED APPLICATIONS

The present application is a national stage filing under 35 U.S.C. § 371 of International Application No. PCT/US2017/027170, filed 12 Apr. 2017, which claims the benefit of priority to U.S. Provisional Application No. 62/321,290, filed 12 Apr. 2016, and U.S. Provisional Application No. 62/382,994, filed 2 Sep. 2016, the contents of each of the foregoing are incorporated herein by reference in its entirety.

STATEMENT OF GOVERNMENT INTEREST

This invention was made with government support under DMR1507810 awarded by the National Science Foundation and DE-AC02-06CH11357 awarded by the U.S. Department of Energy. The government has certain rights in the invention.

FIELD OF INVENTION

The technology generally relates to flexible organic electronic materials. In particular, the technology relates to flexible piezoelectric and ferroelectric haloimidazole crystals.

BACKGROUND

In 1921, Valasek observed that the spontaneous polarisation of Rochelle salt (potassium sodium tartrate tetrahydrate) crystals can be inverted by applying an external electric field. In an attempt to emphasise the conceptual similarity to ferromagnetism, which was already known at the time, the new effect was later named ferroelectricity. In the interim, it has become a workhorse in numerous technologies, finding applications in data and energy storage. In crystals, ferroelectricity is observed only in materials adopting polar space groups, and is accompanied by the related phenomena of piezoelectricity and pyroelectricity, further expanding the applications of ferroelectric materials to piezoelectric actuators, sensors, and transducers. In contrast, antiferroelectricity can also be observed in the much more common centrosymmetric structures in the form of double hysteresis polarisation—electric field profiles consisting of positive and negative field loops when the applied field is sufficiently strong. The sharp change in polarisation and volume as a result of applied field or pressure in these systems has the potential to advance technologies in the fields of energy and sensing.

The most widely used inorganic ferroelectric materials such as perovskite barium titanate and lead zirconate titanate, while showing excellent performance characteristics, are intrinsically limited in their applicability due to the presence of heavy metals. This factor has fuelled the search for more benign substitutes with comparable electric properties. Organic materials have appeared as promising alternatives, and several room-temperature small-molecule organic ferroelectrics and antiferroelectrics have been reported. Aside from other desirable properties, organic materials can theoretically also exhibit flexibility, although in practice most organic ferroelectrics and antiferroelectrics are rigid crystalline solids. The most widely applicable organic materials used in flexible devices are ferroelectric polymers that, when prepared as thin films, are suitable for both ferroelectric and piezoelectric applications.

While it would be desirable to be able to produce organic ferroelectric/antiferroelectric materials that are both crystalline and flexible, identifying such materials is challenging, since both crystal flexibility and ferroelectricity/antiferroelectricity are rather rare properties in of themselves. Commonly encountered motifs in organic ferroelectrics/antiferroelectrics are chains of hydrogen bonds, where hydrogen bond donors and acceptors switch roles under the influence of an applied electrical field. Although the origins of crystal elasticity are poorly understood, the known examples suggest that the elastic and plastic properties might correlate with halogen bonding in the crystals. A search of the Cambridge Structural Database revealed that some halogenated imidazoles both (i) crystallize in polar space groups and (ii) assemble into chains as a result of forming N—H • • • N hydrogen bonds.

Herein we report that suitably designed trisubstituted haloimidazoles display ferroelectricity and piezoelectricity, together with the tendency to produce naturally distorted or elastic crystals, with both electric and mechanical properties arising from distinctly different structural features of these unique molecules.

SUMMARY OF THE INVENTION

Disclosed herein a haloimidazole crystals. The crystal may have one or more of the following properties: piezoelectricity, pyroelectricity, ferroelectricity, flexibility, or any combination thereof. The organic crystals disclosed are suitable for a number of applications, including, but not limited to, data storage, energy storage, or piezoelectric actuators, sensors, or transducers.

The crystals comprise at least one haloimidazole compound of formula I:

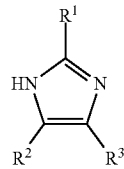

wherein $R^1$, $R^2$, and $R^3$ are independently selected from the group consisting of hydrogen, an alkyl group, and a halogen and wherein at least one of $R^1$, $R^2$, and $R^3$ is a halogen.

In some embodiments, the haloimidazole is a dihaloimidazole. The dihaloimidazole may comprise two different halogens. In other embodiments, the dihaloimidazole comprises two of the same halogen. In some embodiments, one of $R^1$, $R^2$, and $R^3$ is an alkyl group. In particular embodiments, the alkyl group is selected from methyl and ethyl In other embodiments, the haloimidazole is a trihaloimidazole. The trihaloimidazole may comprise at least two different halogens. In other embodiments, the trihaloimidazole comprises three of the same halogen.

For any of the haloimidazoles described above, the halogen may be selected from the group consisting of chlorine, bromine, and iodine.

In particular embodiments, the haloimidazole is selected from the group consisting of 4,5-dichloro-2-methylimidazole, 4,5-dibromo-2-methylimidazole, 4,5-diiodo-2-methylimidazole, 2,4,5-trichloroimidazole, 2,4,5-tribromoimidazole, 2-bromo-4,5-dichloroimidazole, 2,4-dibromo-5- chloroimidazole, 2,4-dibromo-5-methylimidazole, 4,5-dichloro-2-ethylimidazole, 4,5-dibromo-2-ethylimidazole, 2,4,5-triiodoimidazole, and 2-bromo-4,5-dimethylimidazole.

In some embodiments, the crystal comprises at least two different haloimidazole compounds of formula I. In particular embodiments, the at least two different haloimidazole compounds of formula I comprise a first halomidazole and a second haloimidazole and wherein the first haloimidazole is a dihaloimidazole and the second haloimidazole is a trihaloimidazole. The dihaloimidazole may be selected from the group consisting 4,5-dichloro-2-methylimidazole, 4,5-dibromo-2-methylimidazole, 4,5-diiodo-2-methylimidazole, 2,4-dibromo-5-methylimidazole, and 4,5-dichloro-2-ethylimidazole, 4,5-dibromo-2-ethylimidazole. The trihaloimidazole may be selected from the group consisting of 2,4,5-trichloroimidazole, 2,4,5-tribromoimidazole, 2-bromo-4,5-dichloroimidazole, 2,4-dibromo-5-chloroimidazole, and 2,4,5-triiodoimidazole.

The molar ratio of the first haloimidazole to the second haloimidazole may be between 5:1 to 1:5.

Another aspect of the invention is a mixed crystal comprising a first haloimidazole and a second haloimidazole, wherein the first haloimidazole is a compound of formula I:

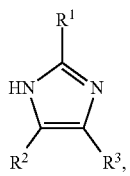

wherein each of $R^1$, $R^2$, and $R^3$ of the first haloimidazole are a halogen,
wherein the second haloimidazole is a compound of formula I:

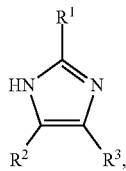

and
wherein $R^1$, $R^2$, and $R^3$ of the second haloimidazole are independently selected from the group consisting of an alkyl group and a halogen and at least two of $R^1$, $R^2$, and $R^3$ are a halogen. $R^1$ of the second haloimidazole may be the alkyl group. In particular embodiments, the alkyl group is a methyl group.

In some embodiments, both $R^2$ and $R^3$ of the second haloimidazole are the same halogen. In particular embodiments, the second haloimidazole is selected from the group consisting of 4,5-dichloro-2-methylimidazole, 4,5-dibromo-2-methylimidazole, and 4,5-diiodo-2-methylimidazole. In other embodiments, both $R^2$ and $R^3$ of the second haloimidazole are different halogens.

In some embodiments, each of $R^1$, $R^2$, and $R^3$ of the first haloimidazole are the same halogen. In particular embodiments, the first haloimidazole is selected from the group consisting of 2,4,5-trichloroimidazole, 2,4,5-tribromoimidazole, and 2,4,5-triiodoimidazole. In other embodiments, one of $R^1$, $R^2$, and $R^3$ of the first haloimidazole is a different halogen than the other two halogens of the first haloimidazole. In particular embodiments, the first haloimidazole is selected from the group consisting of 2-bromo-4,5-dichloroimidazole, 2,4-dibromo-5-chloroimidazole.

The molar ratio of the first haloimidazole to the second haloimidazole may be between 5:1 and 1:5.

Another aspect of the method is for preparing a haloimidazole crystal, the method comprising evaporating a solvent from a solution, the solution comprising the solvent and at least one haloimidazole compound of formula I:

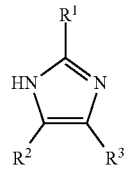

wherein $R^1$, $R^2$, and $R^3$ are independently selected from the group consisting of hydrogen, an alkyl group, and a halogen and wherein at least one of $R^1$, $R^2$, and $R^3$ is halogen.

In some embodiments, the haloimidazole is a dihaloimidazole. The dihaloimidazole may comprise two different halogens. In other embodiments, the dihaloimidazole comprises two of the same halogen. In some embodiments, one of $R^1$, $R^2$, and $R^3$ is an alkyl group. In particular embodiments, the alkyl group is selected from methyl and ethyl In other embodiments, the haloimidazole is a trihaloimidazole. The trihaloimidazole may comprise at least two different halogens. In other embodiments, the trihaloimidazole comprises three of the same halogen.

For any of the haloimidazoles described above, the halogen may be selected from the group consisting of chlorine, bromine, and iodine.

In particular embodiments, the haloimidazole is selected from the group consisting of 4,5-dichloro-2-methylimidazole, 4,5-dibromo-2-methylimidazole, 4,5-diiodo-2-methylimidazole, 2,4,5-trichloroimidazole, 2,4,5-tribromoimidazole, 2-bromo-4,5-dichloroimidazole, 2,4-dibromo-5-chloroimidazole, 2,4-dibromo-5-methylimidazole, 4,5-dichloro-2-ethylimidazole, 4,5-dibromo-2-ethylimidazole, 2,4,5-triiodoimidazole, and 2-bromo-4,5-dimethylimidazole.

In some embodiments, the crystal comprises at least two different haloimidazole compounds of formula I. In particular embodiments, the at least two different haloimidazole compounds of formula I comprise a first halomidazole and a second haloimidazole and wherein the first haloimidazole is a dihaloimidazole and the second haloimidazole is a trihaloimidazole. The dihaloimidazole may be selected from the group consisting 4,5-dichloro-2-methylimidazole, 4,5-dibromo-2-methylimidazole, 4,5-diiodo-2-methylimidazole, 2,4-dibromo-5-methylimidazole, and 4,5-dichloro-2-ethylimidazole, 4,5-dibromo-2-ethylimidazole. The trihaloimidazole may be selected from the group consisting of 2,4,5-trichloroimidazole, 2,4,5-tribromoimidazole, 2-bromo-4,5-dichloroimidazole, 2,4-dibromo-5-chloroimidazole, and 2,4,5-triiodoimidazole.

The molar ratio of the first haloimidazole to the second haloimidazole may be between 5:1 to 1:5.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 8A-8I show SEM images of mixed crystal 1·6 (scale bar 1 mm), 1·6 (scale bar 500 μm), 1·6 (scale bar 100 μm), 2·5 (scale bar 1 mm), 2·5 (scale bar 300 μm), 2·5 (scale bar 50 μm), 2·7 (scale bar 2 mm), 2·7 (scale bar 500 μm), and 2·7 (scale bar 200 μm), respectively.

FIG. 8J shows a schematic of crystal deformation. X • • • X contacts are not shown for the sake of clarity.

FIG. 9A shows a 3D image of the topography in FIG. 9B with the colour map of the long axis lateral phase (FIG. 9D) demonstrating the one-to-one correspondence, and the molecular arrangement in the crystallographic ac plane. FIG. 9C shows lateral amplitude of the long axis of the crystal. FIG. 9D shows lateral phase of the long axis response. Scale bars in FIGS. 9B-9D are 470 nm.

FIG. 9E shows a topography image of another section of the same crystalline needle after rotating the sample 90 degrees. FIG. 9F shows the lateral amplitude and FIG. 9G shows the lateral phase response of the short axis of the crystal.

FIGS. 9J-9L show PFM images of a larger crystal of compound 2 than for FIGS. 9A-9G. A topography image of the large crystal of 2 is shown in FIG. 9J. FIG. 9K shows lateral amplitude of the long axis of the crystal. FIG. 9L shows lateral phase of the long axis response. Scale bars are 1 μm in FIGS. 9J-9L.

FIGS. 9M-9O show PFM images of a larger crystal of compound 2 than for FIGS. 9A-9G. A topography image of the large crystal of 2 is shown in FIG. 9M. FIG. 9N shows vertical amplitude and FIG. 9O shows vertical phase response of the crystal. Scale bars are 1 μm in FIGS. 9M-9O.

FIGS. 10A-10D show PFM images of the vertical amplitude, vertical phase, lateral amplitude, and lateral phase of the long axis response of the crystal, respectively. The scale bars are 10 μm. FIG. 10E shows a 3D schematic of the domain structure in the crystal imaged by PFM. FIG. 10F shows the lateral amplitude and lateral phase hysteresis loops obtained by a pulse dc mode. FIG. 10G shows the vertical amplitude and vertical phase hysteresis loops obtained by a pulse dc mode. FIG. 10H shows the lateral amplitude and phase and FIG. 10I shows the vertical amplitude and phase hysteresis loops obtained by a continuous dc mode.

FIGS. 11A-11B shows lateral amplitude and phase images of the crystal, respectively. The scale bars are 5 μm. FIGS. 11C-11D show lateral piezoresponse amplitude and phase hysteresis loops obtained by a pulse dc mode.

DETAILED DESCRIPTION

Figure 1A:
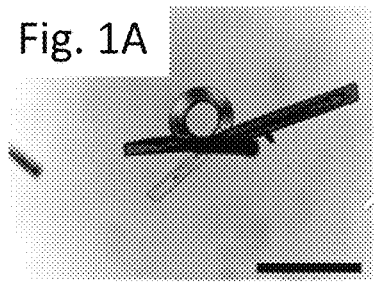
FIGS. 1A-1L show optical microscopy images of crystals of compounds 1-12, respectively (Scale bar 500 μm).
Figure 1B:
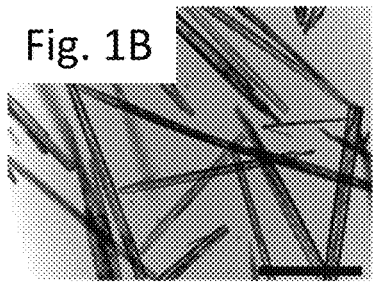
Figure 1C:
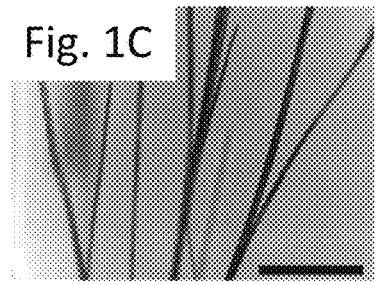
Figure 1D:
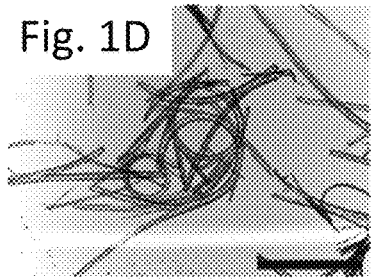
Figure 1E:
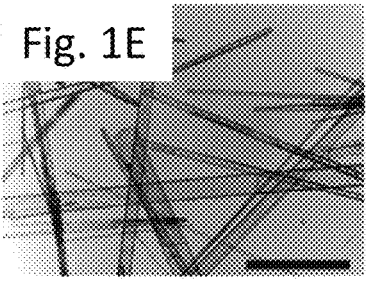
Figure 1F:
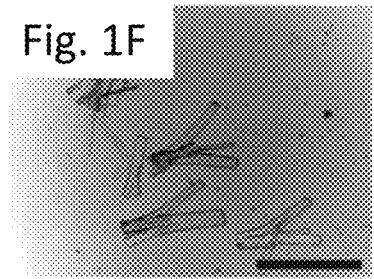
Figure 1G:
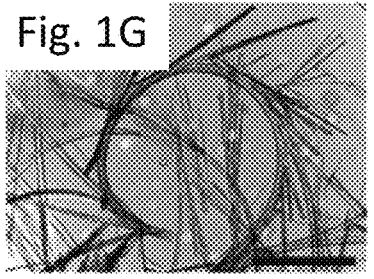
Figure 1H:
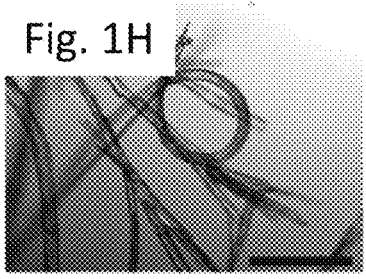
Figure 1I:
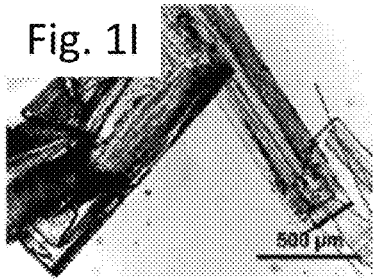
Figure 1J:
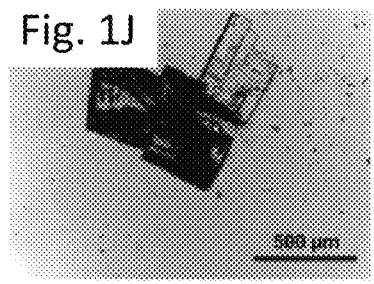
Figure 1K:
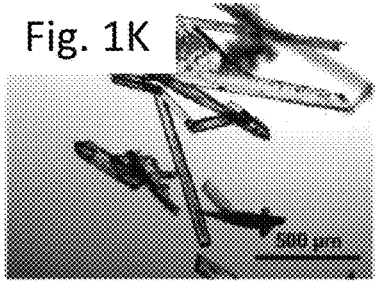
Figure 1L:
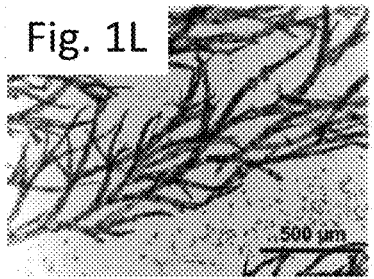

Disclosed herein are haloimidazoles and organic crystals comprising one or more haloimidazoles. The crystal may be flexible, piezoelectric, pyroelectric, ferroelectric, or any combination thereof. The organic crystals disclosed are suitable for a number of applications, including, but not limited to, data storage, energy storage, or piezoelectric actuators, sensors, or transducers.

Haloimidazoles of the present invention comprise an imidazole having at least one halogen substituent on the imidazole ring. In some embodiments, the substituted haloimidazole has a general formula

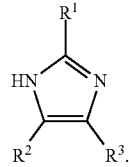

and R$^1$, R$^2$, and R$^3$ may be independently selected from the group consisting of hydrogen, an alkyl group, and a halogen where at least one of R$^1$, R$^2$, and R$^3$ is halogen. In some embodiments, the substituted haloimizadole is a dihaloimidazole where both R$^1$ and R$^2$, both R$^1$ and R$^3$, or both R$^2$ and R$^3$ are halogens. In other embodiments, the substituted haloimidazole is a trihaloimidazole, where each of R$^1$, R$^2$, and R$^3$ are halogens. The halogen may be chlorine, bromine, or iodine. The alkyl group may be a methyl group or an ethyl group. In certain embodiments, R$^1$, R$^2$, and R$^3$ are independently selected from hydrogen, methyl, ethyl, chlorine, bromine, and iodine. In particular embodiments, the substituted haloimidazole is:

(compound 1)
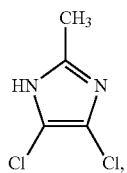

(compound 2)
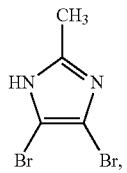

(compound 3)
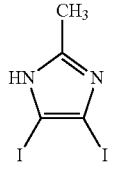

(compound 4)
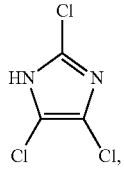

(compound 5)
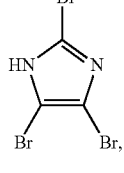

(compound 6)
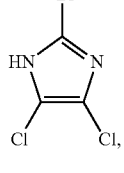

(compound 7)
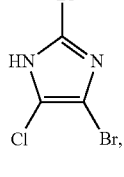

(compound 8)
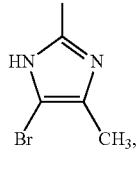

(compound 9)
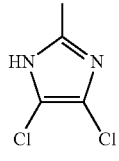

(compound 10)
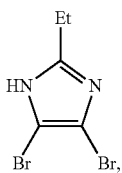

(compound 11)
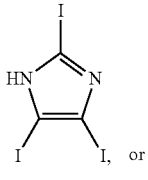

or (compound 12)
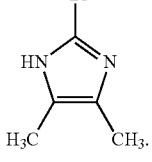

Names for compounds 1-12 are as follows: 4,5-dichloro-2-methylimidazole (1), 4,5-dibromo-2-methylimidazole (2), 4,5-diiodo-2-methylimidazole (3), 2,4,5-trichloroimidazole (4), 2,4,5-tribromoimidazole (5), 2-bromo-4,5-dichloroimidazole (6), 2,4-dibromo-5-chloroimidazole (7), 2,4-dibromo-5-methylimidazole (8), 4,5-dichloro-2-ethylimidazole (9), 4,5-dibromo-2-ethylimidazole (10), 2,4,5-triiodoimidazole (11), and 2-bromo-4,5-dimethylimidazole (12).

In some embodiments, the crystal may comprise a haloimidazole as described above. In the Examples that follow, crystals prepared from compounds 1-12 are described. In other embodiments, the crystal may comprise two or more different haloimidazoles forming a mixed crystal (i.e., solid solution). In the Examples that follow, crystals prepared from solid solutions of 1·4, 1·5, 1·6, 1·7, 2·6, and 2·7 are described. Where the crystal comprises two or more haloimidazoles, the molar ratio between the different haloimidazoles may be any suitable molar ratio between the haloimidazoles. In some embodiments, the molar ratio of the first compound to the second compound may be between about 5:1 and about 1:5, including from about 2:1 to about 1:2 or about 1:1. In the Examples that follow, mixed crystals having molar ratios of 2:1 and 1:1 were prepared and described.

Crystals may be prepared from the haloimidazole crystals described above. The crystals may have at least one property of the following properties: piezoelectricity, ferroelectricity, or flexibility. In some embodiments, the crystals have two or more of the above properties. In particular embodiments, the crystals have all three of those properties.

As used herein, a material possesses the property of "flexibility" if it has an elastic modulus less than about 0.5 GPa, a hardness less than less than about 100 MPa, or both. In some embodiments of the invention, the crystals described herein have an elastic modulus less than about 0.5. GPa, including crystals having an elastic modulus less than 0.45, 0.40, 0.35, 0.30, 0.25, 0.20, 0.15, or 0.10 GPa. In some embodiments of the invention, the crystals described herein have a hardness less than about 100 MPa, including crystals having a hardness less than 95 MPa, 90 MPa, 85 MPa, 80 MPa, 75 MPa, 70 MPa, 65 MPa, 60 MPa, 55 MPa, 50 MPa, 45 MPa, or 40 MPa. In particular embodiments, the crystals described herein have an elastic modulus less than about 0.5 GPa and a hardness less than about 100 MPa.

Crystal preparation. The crystals comprising the haloimidazole may be prepared by any suitable method for crystal preparation. In some embodiments, the method for preparing a substituted haloimidazole crystal comprises evaporating a solvent from a solution, the solution comprising the solvent and one or more haloimidazoles. In certain embodiments, the solution comprises the solvent and two or more haloimidazoles. In the Examples that follow $Me_2CO/H_2O$ mixtures were used, but other volatile solvents and/or mixtures of solvents suitable for crystallization may be used. Examples of solvents suitable for use for crystallization include of water, methanol, acetone, acetonitrile, and combinations thereof.

Crystal morphology and structure. Remarkably, the crystals of these haloimidazole compounds exhibited substantial natural distortions, sometimes appearing as spirals making multiple full turns or needle-like. Crystals comprising haloimidazoles were characterised by single-crystal X-ray diffraction. (Table 1) This allows for the identification of a group of isostructural compounds displaying very different crystal morphologies. While the symmetrically substituted imidazoles 2, 3 and 5 formed needle-like crystals, the symmetrically chlorinated imidazoles 1 and 4, as well as the unsymmetrically substituted compounds 6, 7, and 8 behaved quite differently. (See FIGS. 1A-1H showing crystals obtained from compounds 1-12, respectively.)

The crystals of these haloimidazoles may crystalize in a noncentrosymmetric space group. In some embodiments, the haloimidazoles crystallize in polar, noncentrosymmetric space groups. Of the 21 noncentrosymmetric space groups, 20 are piezoelectric. (See, Table 2.) The exception is the 432 cubic class. Piezoelectricity is the property of materials to develop electric displacement that is proportional to an applied mechanical stress and, conversely, they deform under application of an electric field. Among the 20 piezoelectric classes, there are ten pyroelectric groups that posses a unique polar axis, i.e., the polar groups. Pyroelectric crystals contain a built-in polarization that manifests itself in temperature-induced changes in the total dipole moment of the unit cell. If spontaneous polarization can be reversed by an external electric field, the crystal is ferroelectric. As a result these haloimidazoles forming crystals having noncentrosymmetric and, more specifically, polar-noncentrosymmetric space groups, the crystals may be piezoelectric, piezoelectric and pyroelectric, or piezoelectric, pyroelectric and ferroelectric.

Figure 2:
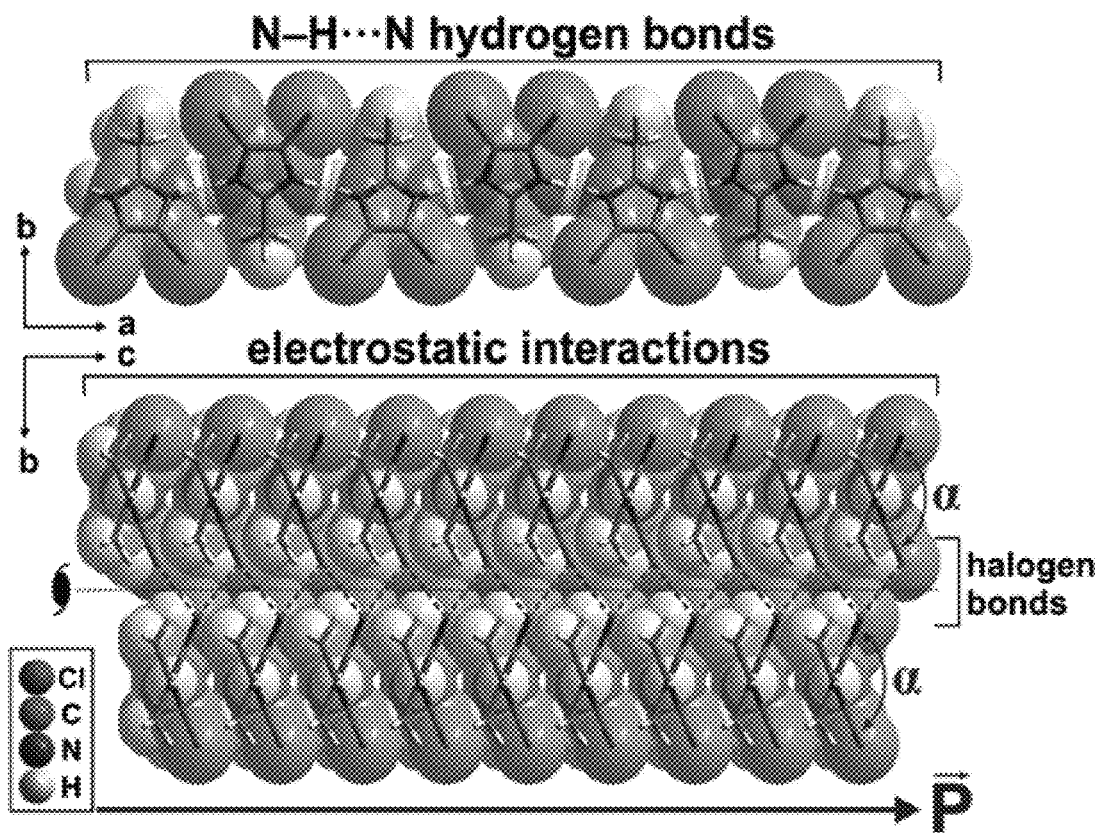
FIG. 2 shows intermolecular interactions present in the crystal structures.
Figure 3A:
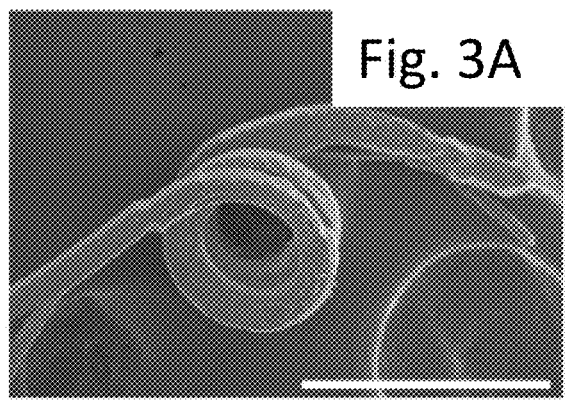
FIGS. 3A-3D show SEM images highlighting the microstructure of the crystals of compound 1 (Scale bars 300 μm, 10 μm, 100 μm, and 40 μm, respectively).
Figure 3B:
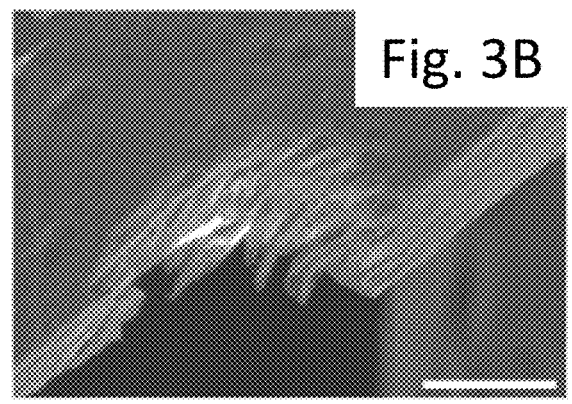
Figure 3C:
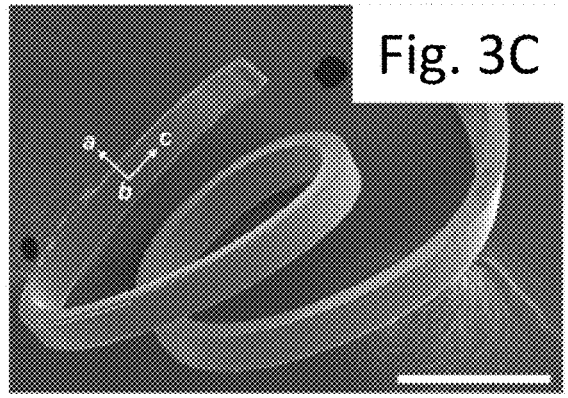
Figure 3D:
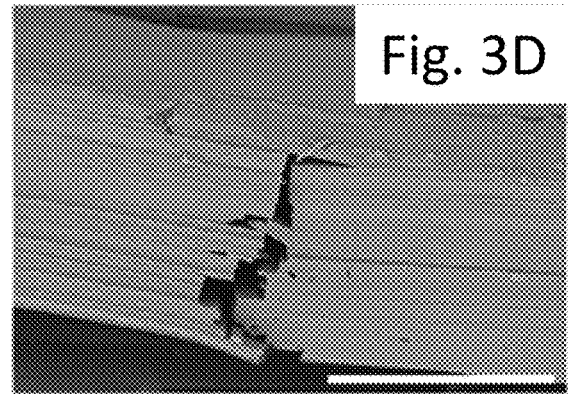

The crystallographic data reveal that all compounds 1-8 crystallise in the orthorhombic Ama2 space group (Laue group mm2) with a short c-axis of ca. 4 Å, a situation which is characteristic of small halogenated aromatic compounds. A thorough analysis of their crystal structures reveals highly anisotropic intermolecular interactions which have been identified as a distinctive feature of plastic crystals. The crystal packing is governed by three types of interactions of different strengths, namely (i) N—H • • • N hydrogen bonds (2.84-2.97 Å) linking imidazole molecules in infinite chains extending in the a-axis direction, (ii) electrostatic interactions leading to the stacking of the chains one above the other along the c-axis to form sheets with the interchain distance between the imidazole rings in the range of 3.79-4.42 Å, and (iii) halogen-halogen interactions (Type II, see below) holding these sheets together. (See, e.g., FIG. 2) The anisotropy of the crystal packing forces translates itself to the crystal microstructure. Images obtained by scanning electron microscopy (SEM) reveal the layered structures of the crystals in the dimension perpendicular to the be planes. (See, e.g., FIGS. 3A-3D)

Figure 4:
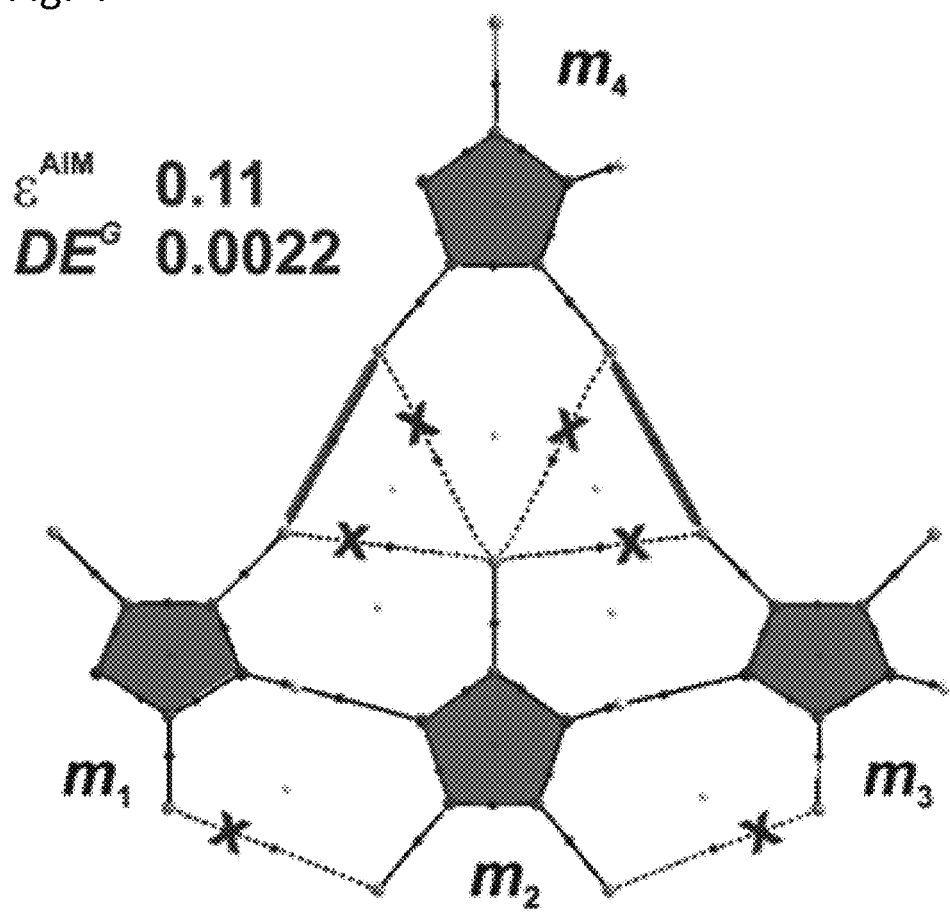
FIG. 4 shows a representative fragment of a solid-state structure of compound 1 showing bond paths (dashed lines) obtained by AIM analysis. Bold lines denote significant interactions whose existence was confirmed by the AIM method, along with their $\varepsilon^{AIM}$ [a.u.] and $DE^G$ [kcal mol$^{-1}$] values.

Computational analysis of intermolecular interactions. Since we suspected that the ability of the trisubstituted haloimidazole crystals to become deformed during growth might arise from weak halogen-halogen contacts, these interactions were investigated computationally. Identifying bond critical points by Atoms in Molecules (AIM) analysis suggests that only halogen-halogen contacts between the molecules related by a 2-fold screw axis ($m_1$ and $m_4$, and $m_4$ and $m_3$ in FIG. 4) are essential, and that the strength of the interaction increases with the growth in the atomic radius of the halogen (Table 3). The geometric parameters of these essential contacts, $\theta_1$ and $\theta_2$ angles (Table 4), allow us to classify them as Type II halogen-halogen interactions ($|\theta_1-\theta_2|\geq 30°$) which, according to the IUPAC definition [Desiraju, G. R. et al. Definition of the halogen bond (IUPAC Recommendations 2013). *Pure Appl. Chem.* 85, 1711-1713, (2013)], are true halogen bonds.

In order to assess the role of these interactions in the structure, the ellipticity ($\epsilon^{AIM}$) and the dissociation energies ($DE^G$) of the bonds were compared to those in hexachlorobenzene $C_6Cl_6$, which is known to form plastic crystals that are easily deformable under the influence of external mechanical forces. According to this analysis, the fragment of $C_6Cl_6$ solid-state structure shown has only two true halogen bonds, with the rest of halogen-halogen interactions being attributed to close packing. Hence, the weakness of these intermolecular interactions explains the ease with which the stacks of $C_6Cl_6$ molecules can glide past each other to alleviate strain, resulting in the plastic deformation of the crystals.

In contrast, the presence of one-dimensional infinite chains composed of imidazole molecules interconnected by hydrogen bonds prevents the gliding between the individual stacks, consistent with the absence of plasticity. In those cases where the halogen bonds are sufficiently weak, as in imidazoles possessing chlorine atoms in positions 4 and 5, the energetic cost of rotation of imidazole rings about the N—H • • • N bonds during crystal growth appears to be low, resulting in a change of a dihedral angle (see FIG. 2) and a local loss of periodicity. This misalignment, which alternatively can be thought of as the dislocation along the 2-fold screw axis (FIG. 2), induces a slight curvature of the halogen-layered sheets, leading to crystal curving on the macroscopic scale. Similar arguments can be used to rationalise the curved crystal morphology observed in the case of 2,4-dibromo-5-methylimidazole (8), where the density of halogen bonds holding the sheets together is lower on account of the presence of the 5-Me substituent, even despite the stronger Br • • • Br bonds.

Figure 5A:
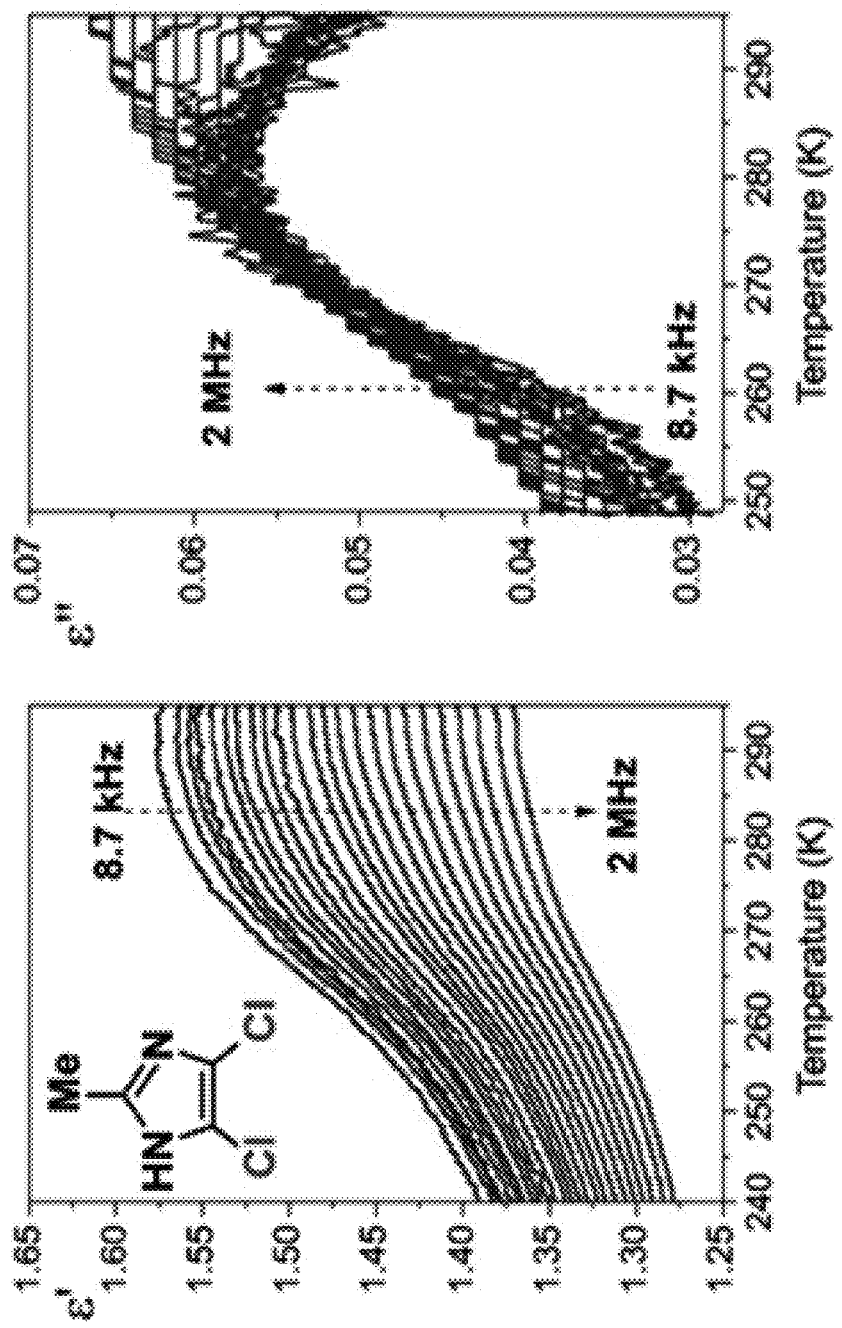
FIGS. 5A-5C show temperature dependence of the real, $\varepsilon'(T)$, and imaginary, $\varepsilon''(T)$, parts of the complex electric permittivity measured for compounds 1, 2, and 3.
Figure 5B:
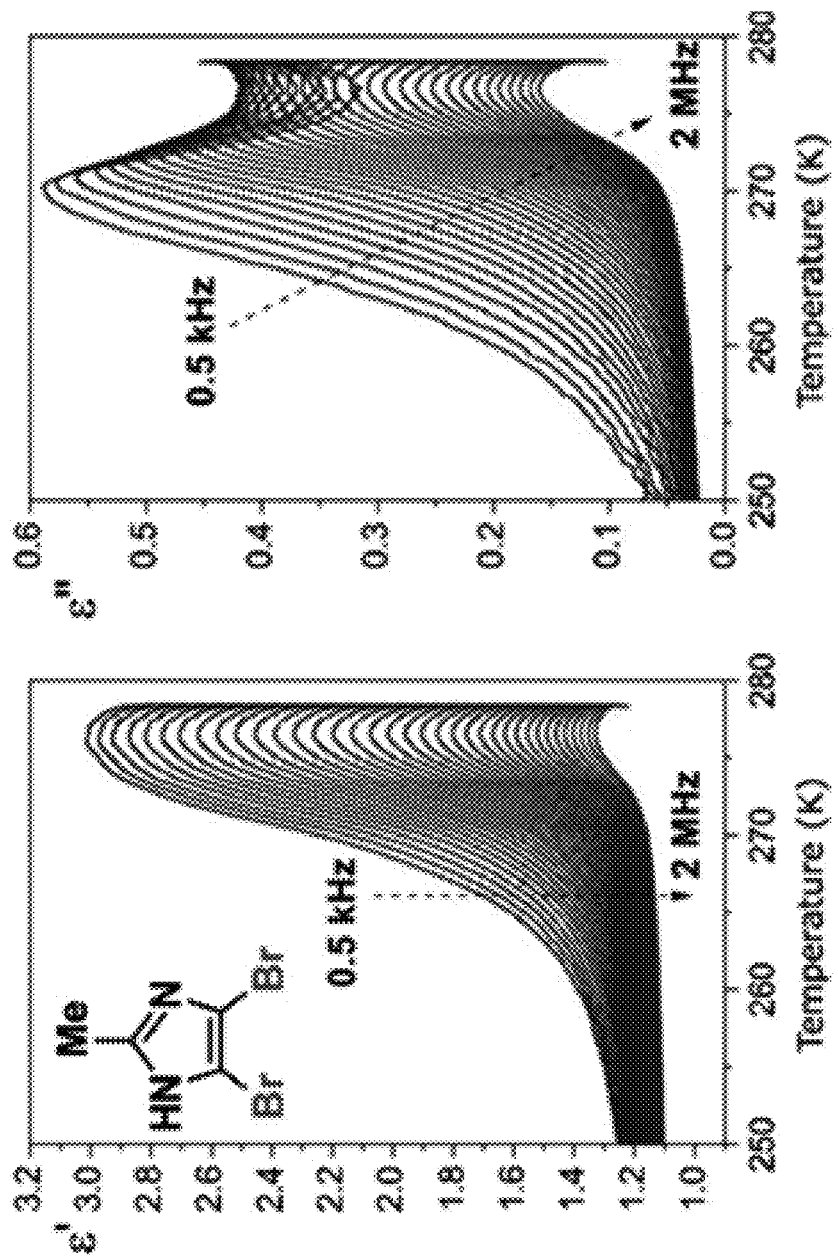
Figure 5C:
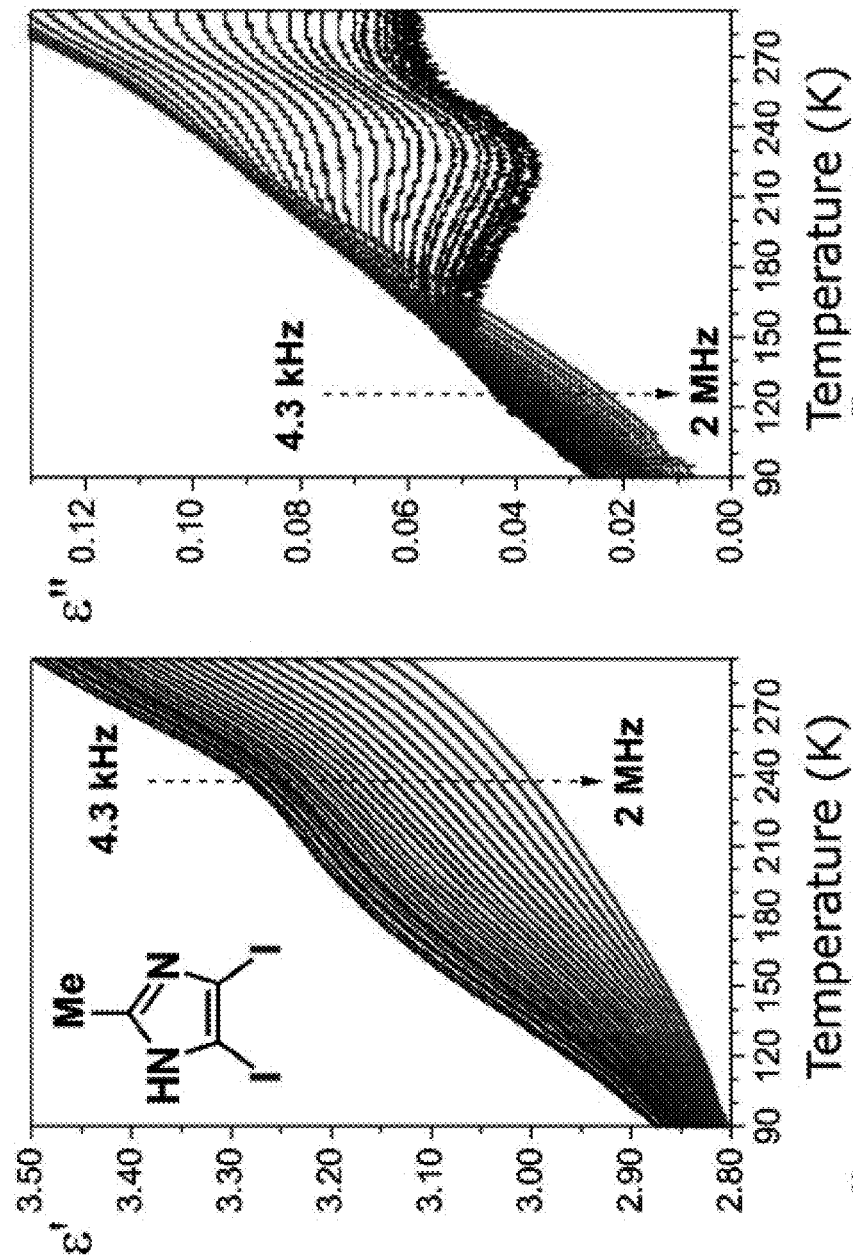
Figure 6A:
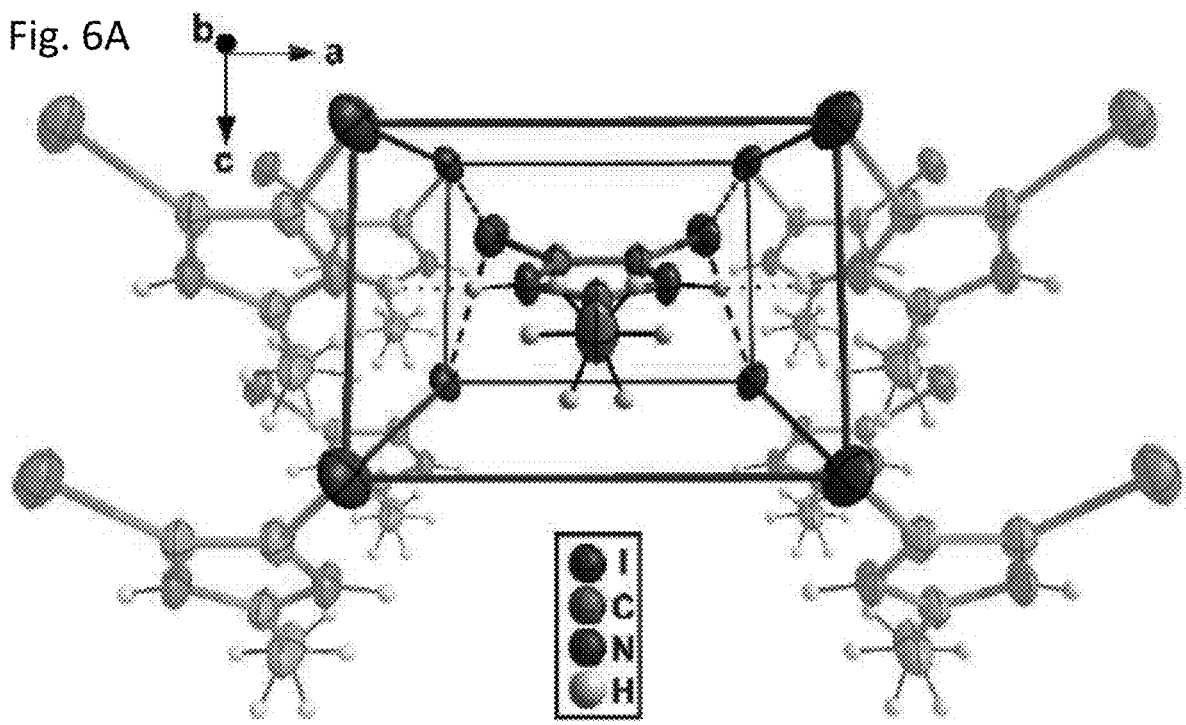
FIGS. 6A-6B show the closest environment of the 4,5-diiodo-2-methylimidazole (3) molecules in the crystal lattice (FIG. 6A) and the comparison of its molecular structure at 250K and 100K (FIG. 6B). Thermal ellipsoids are shown at 50% probability.
Figure 6B:
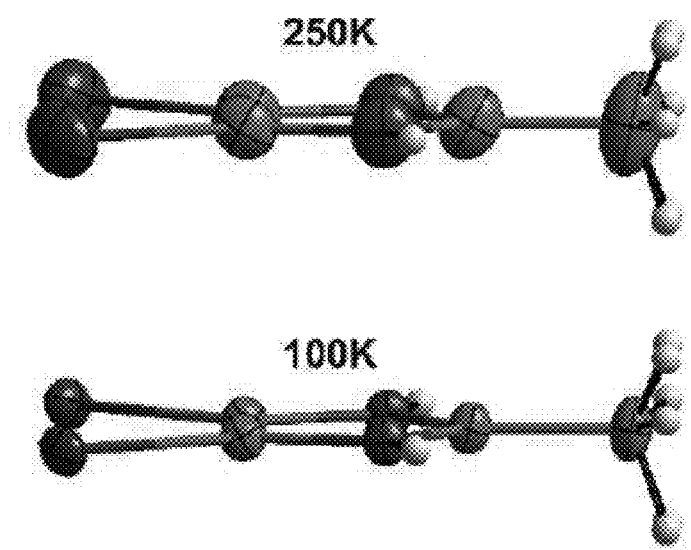

Molecular mobility in the solid state. While formation of curved crystals appears to indicate the ease with which the haloimidazole molecules can be displaced during the crystal growth, it was also of interest to find out whether the molecular mobility is retained in the solid state. Hence, we performed electric permittivity measurements on a few 4,5-dihalo-2-methylimidazoles, specifically 1, 2 and 3. Since the molecules possess permanent dipole moments, the dynamic processes in the crystal can be expected to reveal themselves under the influence of an alternating electric field, provided sufficient space is available in the crystal lattice. Indeed, relaxation processes were observed in the frequency range between 200 Hz and 2 MHz for all three compounds under investigation, as suggested by dispersion and absorption on $\epsilon'(T)$ and $\epsilon''(T)$ curves, respectively (FIGS. 5A-5C). The processes are well described by the Cole-Cole or Havriliak-Negami equations (Tables 6 and 7), and the parameters derived from these equations allowed us to estimate the activation energies $E_a$, which were found to be in the 2.5 to 53 kcal mol$^{-1}$ range. A plausible rationale for the observed relaxation behaviour in the solid state is that certain molecular motions are not fully restrained by the immediate surroundings (see, e.g. FIGS. 6A-6B) of the haloimidazole molecules. The measurements were performed on pelleted samples containing large numbers of randomly oriented crystals. The calculated activation energies show no simple correlation with the expected strengths of the halogen bonds. Rather, the observed dielectric response should be used as a qualitative proof for the existence of substantial molecular mobility in the crystals. Thus, it appears that, while the curved crystal shape is primarily determined by the strength of the halogen bonds, the dynamic processes in the crystal are independent of their morphology, and were observed in both curved (1) and regular (2 and 3) crystals. This realisation leads us to the conclusion that the electrical properties arising from the non-centrosymmetric crystal structure of these haloimidazole systems should persist regardless of the morphological effects that dictate the crystal shape.

Figure 7:
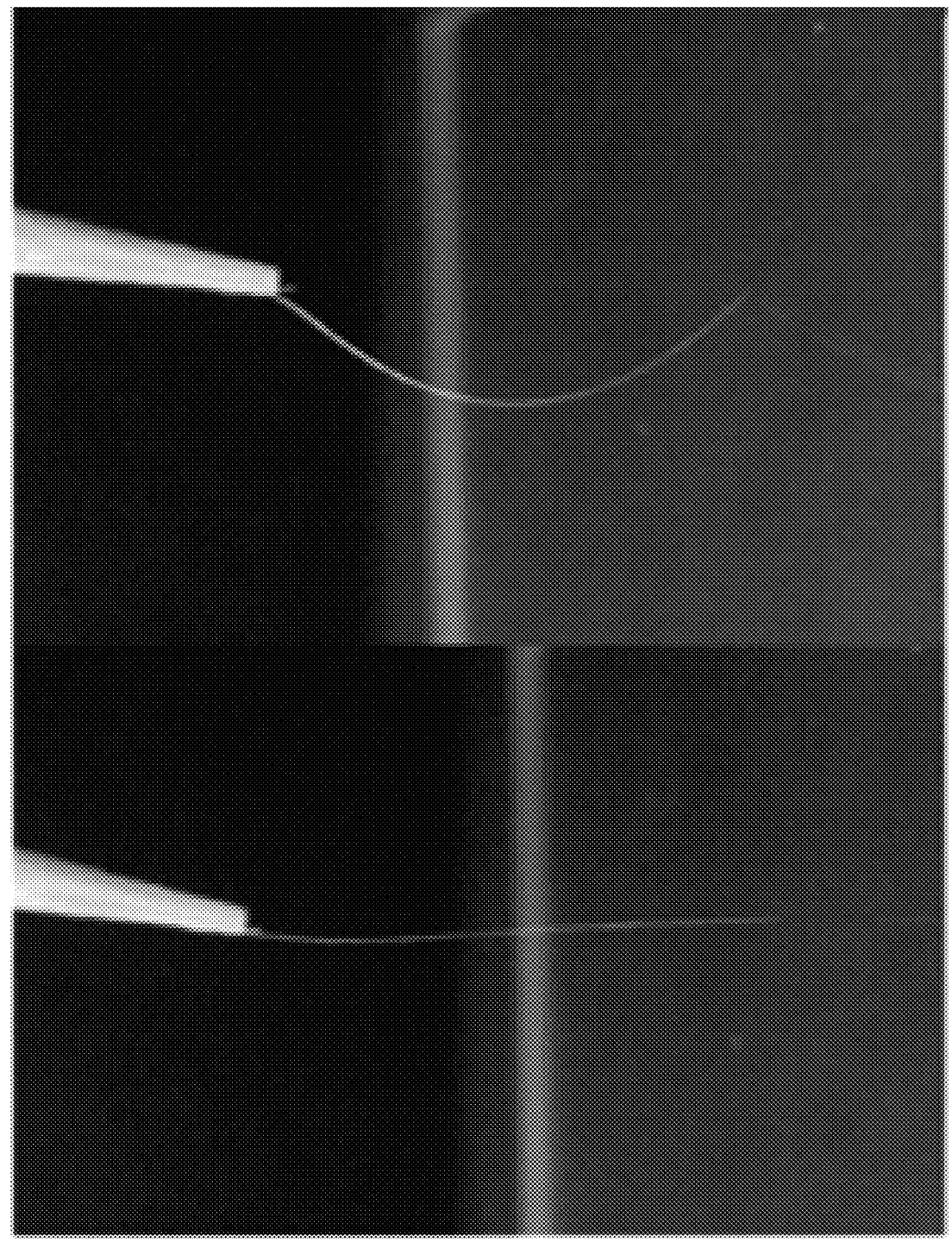
FIG. 7 shows a crystalline needle of a solid solution grown from a Me$_2$CO/H$_2$O mixture and its elastic property.

Flexible mixed crystals. The pursuit of more dynamic morphological properties led us to explore mixed crystal systems. The halogen bonding influence on crystal shape, as well as the molecular mobility of haloimidazoles in the solid state, appeared to us to be convenient handles for tuning the morphology and mechanical properties of the crystals. We proposed that the halogen bonded network of trihaloimidazoles could be disturbed in a controlled manner with the alkyl groups of 4,5-dihalo-2-alkylimidazoles through co-crystallisation in different molar ratios between the two components (Table 8), preventing crystal distortion during growth. In the Examples below, combinations of trihaloimidazoles 4-7 and 4,5-dihalo-2-alkyllimidazoles 1 and 2 were co-crystallized and analysed. Indeed, with some tuning of the component ratio, co-crystallisation typically resulted in formation of 1-4 cm long straight needles, even in those cases (1, 4, and 7) where individual compounds gave curved crystals. According to single-crystal X-ray diffraction (Table 9), the samples prepared by co-crystallisation are not true co-crystals, but rather are mixed crystals (solid solutions) maintaining the ratio of components used for crystallisation. As an additional proof of the structural composition of the mixed crystals (1·5, 1·6, 1·7, 2·5, 2·6, 2·7), and the consistency of the imidazole ratio throughout the crystallisation batch, we performed a series of HPLC experiments (Tables 10-15) with five randomly selected crystals from each batch. Perhaps the most significant aspect of these mixed crystals is the fact that aside from their different morphologies, they were also found to be substantially more flexible than the crystals of pure imidazoles. (See, e.g., FIG. 7.) Thus, when taken out of the crystallisation dish using a toothpick, and pressed against a glass slide, the crystals can be bent many times without breaking, provided that the applied force does not exceed a certain limit. The elastic properties are most visible to the naked eye if the crystal thickness does not exceed 50 μm, and under optimum circumstances the opposite ends of the elastic needle can be forced to touch without breaking the crystals. The solid solutions were analysed with a nanoindentation technique, and determined to be gel-like from their measured hardness, supporting the flexibility observations (Table 16). In order to assess the extent of the structural changes occurring in elastic crystals, we performed an X-ray diffraction study of a crystal that had been exposed to multiple bending/relaxation cycles. Since no elongation of X-ray diffraction peaks was observed, and the peaks could be indexed to the unit cell identical to that of the crystal prior to bending, it can be assumed that the molecules regain their original positions in the crystal lattice upon withdrawal of the applied bending force.

Based on the crystal indexing data and SEM imaging, we were able to propose a mechanism for the observed crystal flexibility. Attaching bent elastic crystals to carbon tape used as the SEM substrate, followed by fracturing the mechanically strained crystals, allowed us to acquire SEM images clearly demonstrating the exposed layers in the crystal corresponding to the N—H • • • N chains expanding in the a-axis direction (see, e.g., FIGS. 8A-8I). Thus, it seems likely that it is the facile slippage of the imidazole chains past each other in the ab plane—distorting electrostatic interactions between imidazole rings in the c-axis direction—that confers flexibility upon the mixed crystals (FIG. 8J). The ability of the crystals to deform elastically in response to the bending force appears to be a function of the X • • • X halogen bonds wherein the potential wells seems to be wide enough to allow the bonds become strained/relaxed without being broken. When the external force is removed, the bonds regain their original position, causing the crystal to bounce back and adopt its original shape.

Piezoelectric and ferroelectric properties. Initial electromechanical experiments for determining the piezoelectric nature of the materials were carried out using Piezoresponse Force Microscopy (PFM) as the method of choice to (i) characterise the electrical behaviour of these systems while (ii) simultaneously defining the topographical orientation of the substrate. The oscillation of the conductive cantilever in contact with a piezoelectric system is captured by both the amplitude and the phase of the collective material and the cantilever system. While the amplitude allows us to examine the magnitude of the piezoelectric response, the phase gives us information on the sequence of the mechanical oscillation that is related to the orientation of the polarization, allowing us to identify domain structures. More specifically, the piezoelectric coefficient, d, is related linearly to the spontaneous polarization, $P_s$, permittivity, ε, electrostrictive coefficient, Q, by Eq. (1)

$$d = 2\varepsilon Q P_s \qquad (1)$$

As ferroelectricity is defined by its switchable polarization by external field, PFM hysteresis loop measurement is a tool that could probe the ferroelectricity if all the potential artifacts are taken care of. Since the cantilever has only two degrees of freedom—vertical bending and lateral torsion—with which to probe the piezoelectric motion of the sample, physical alignment of either the long or short in-plane axes of the crystalline needle with the torsion of the cantilever was performed by rotating the sample through 90 degrees in order to obtain the alternate axis.

Since the crystal face indexing of 1-8 and solid solutions of these molecules differs in regards to the position of the crystallographic a and b axes, we investigated the electromechanical properties of two types of crystals: one with the widest (010) face (crystals of 2) and the other with the widest (100) face (mixed crystals 2·7 and crystals of 8).

Figure 9A:
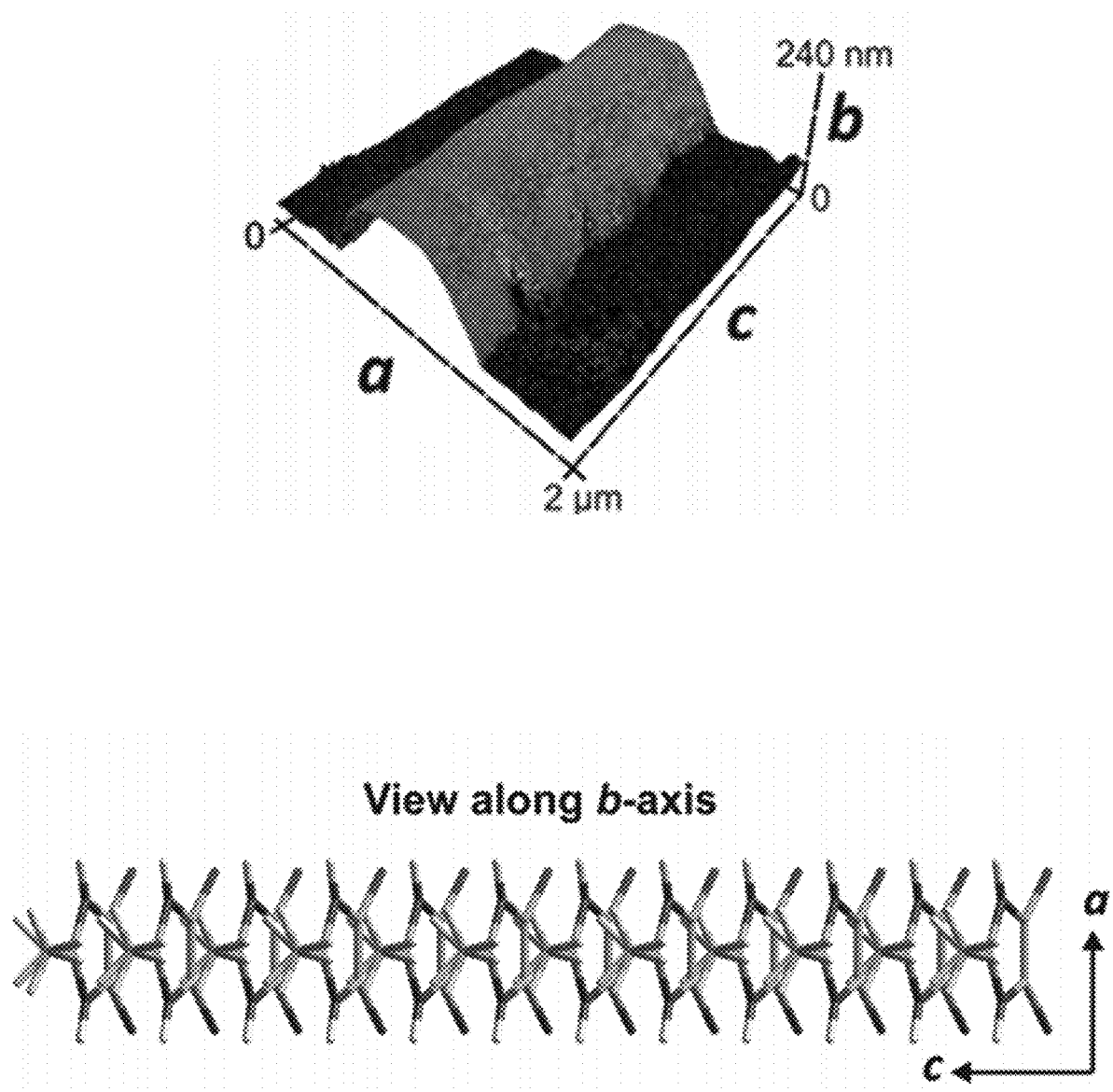
FIGS. 9A-9D show Piezoresponse Force Microscopy (PFM) images along the long axis of a crystal of compound 2.
Figure 9B:
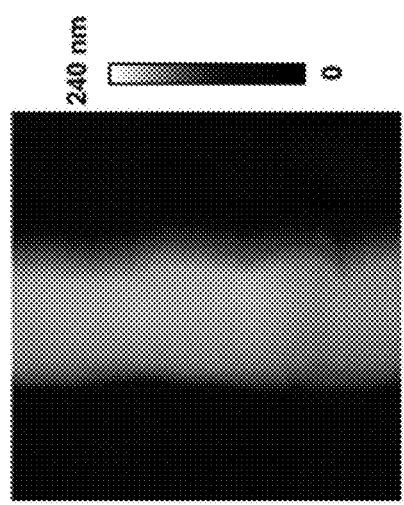
Figure 9C:
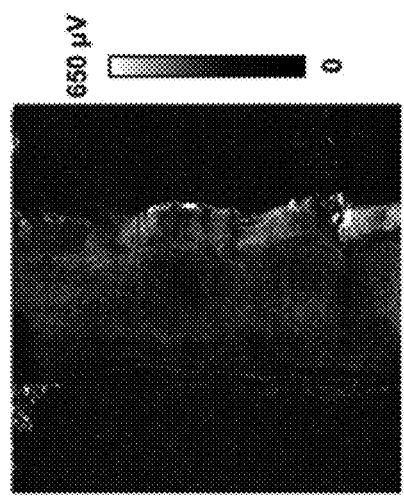
Figure 9D:
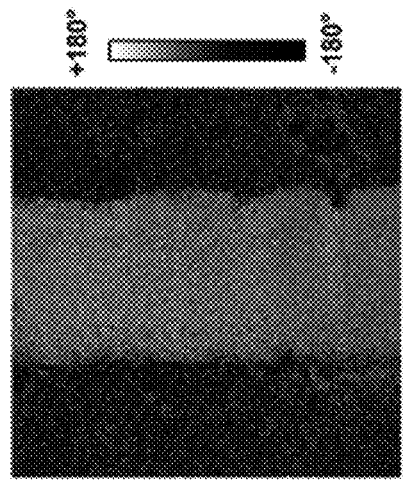
Figure 9E:
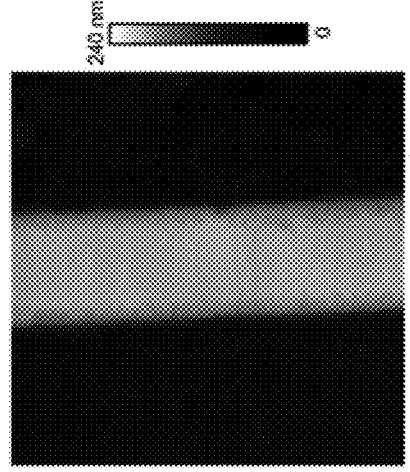
FIGS. 9E-9G show PFM images along a short axis of a different section of the same crystal of compound 2 as in FIGS. 9A-9D.
Figure 9F:
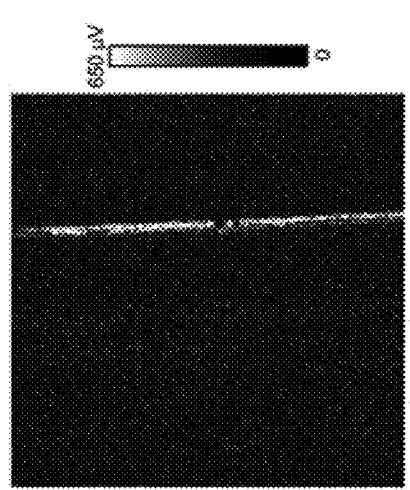
Figure 9G:
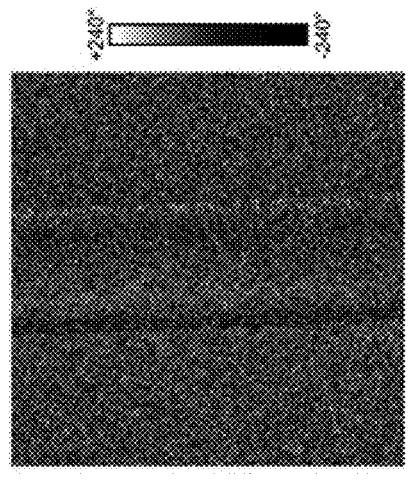
Figure 9H:
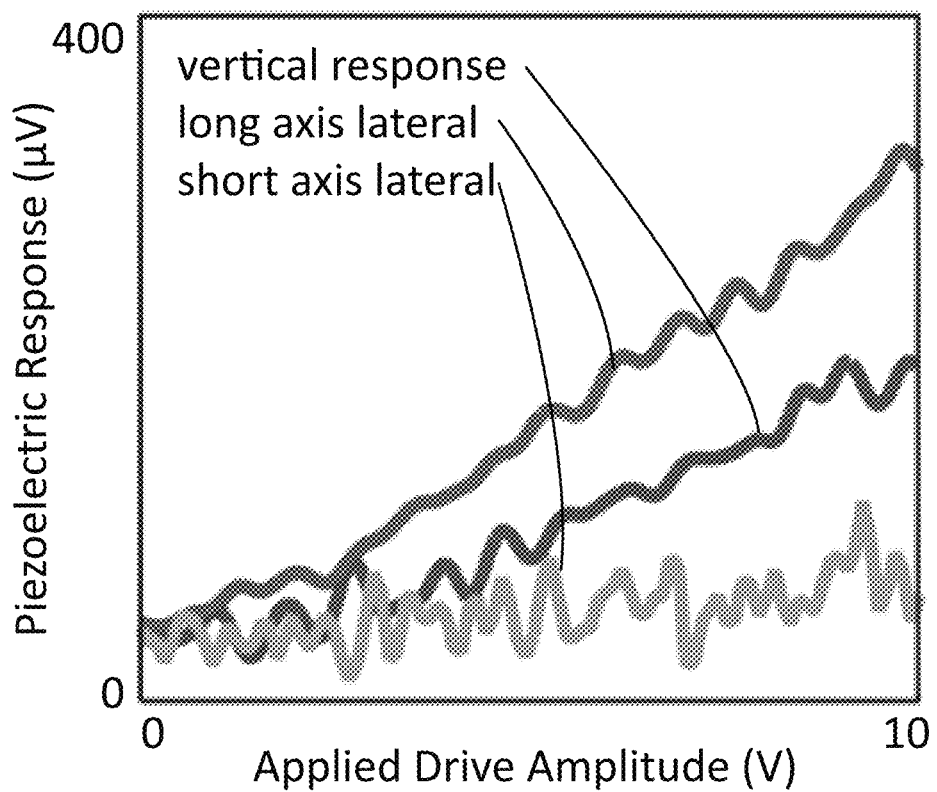
FIGS. 9H-9I show the piezoresponse of 2 and 7 along three crystallographic directions, respectively. The voltage dependence of the piezoresponse of the various axes of the nanocrystal for 2 and 7 demonstrating the linear piezoelectric effect and dominance of the long axis piezoelectric effect.
Figure 9I:
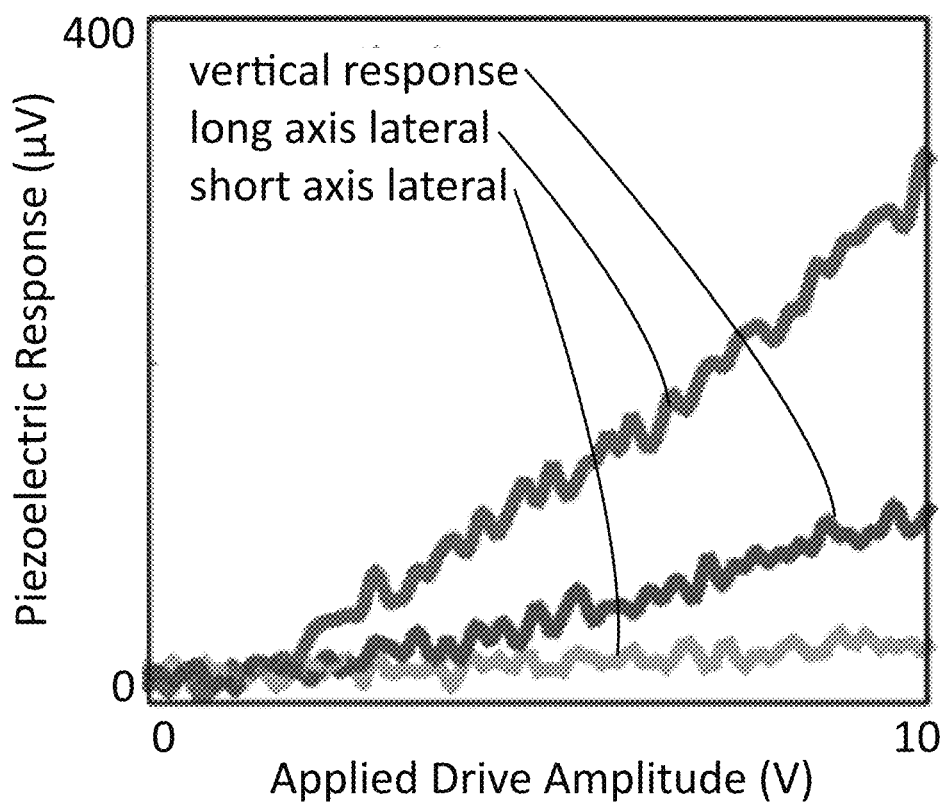
Figure 9P:
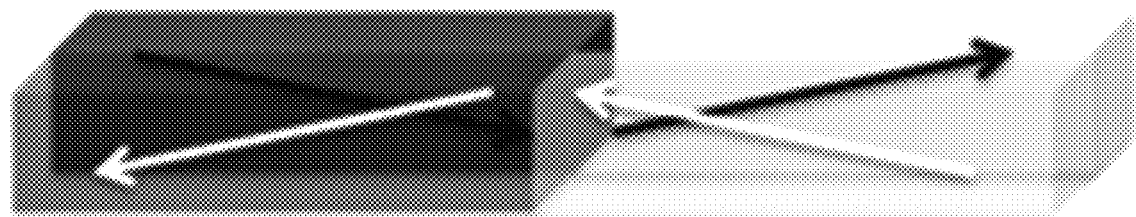
FIG. 9P shows 3D schematic representation of the domain structure in the crystal imaged by PFM.

FIGS. 9A-9B show 3D and 2D topography images, respectively, of the analysed crystal of 2 along with crystallographic directions obtained from the X-ray crystal face indexing. As can be observed, there is a strong amplitude response along the long axis of the crystal (FIG. 9C) and a uniform lateral phase (FIG. 9D). In contrast to the in-plane long axis, the piezoelectric response along the short axis, which is aligned with the primary crystallographic polar axis (c-axis in Ama2 space group) is effectively zero. (See, FIGS. 9E-G.) By ramping the applied drive amplitude and monitoring the response of the material, the piezoelectric properties were probed quantitatively (FIGS. 9H-9I). A linear piezoelectric response is obtained predominantly along the long axis, with a slight piezoelectric response along the vertical dimension as well. Accounting for the background signal, calibrating the vertical deflection signal, and estimating the lateral deflection sensitivity (Table 17), the vertical piezoelectric and long axis lateral effective piezoelectric coefficients for 2 were roughly estimated to be 0.12 and 2.6 pm $V^{-1}$, respectively, however these values may be underestimated as a result of unavoidable friction and slip between the cantilever and the sample. When larger crystals of 2 were analysed, we started to see polarization domain structures with opposite directions as shown in FIGS. 9J-9P. However, both out-of-plane and in-plane piezoresponse did not show any polarization switching characteristics, indicative of piezoelectricity without ferroelectricity or ferroelectric polarization pinned by charged defects.

Figure 10A:
FIGS. 10A-10I show polarization domain and piezoresponse hysteresis loops of 2·7.
Figure 10B:
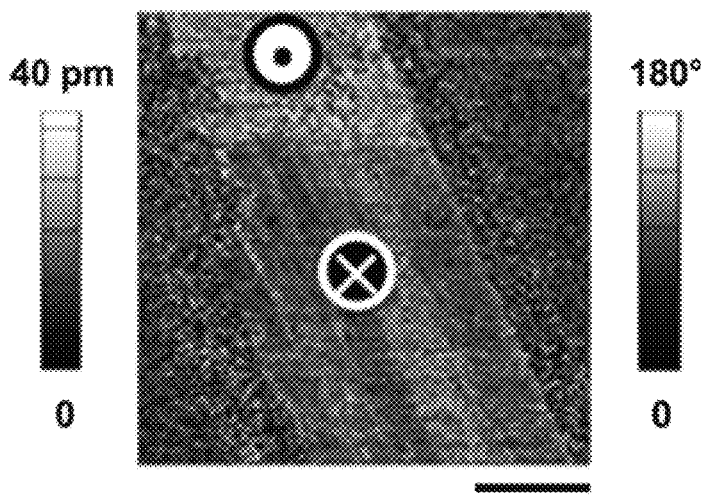
Figure 10C:
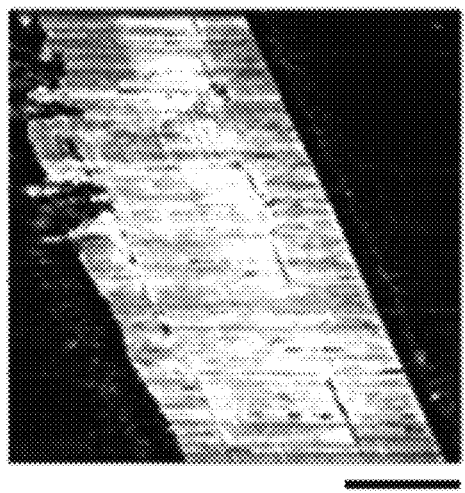
Figure 10D:
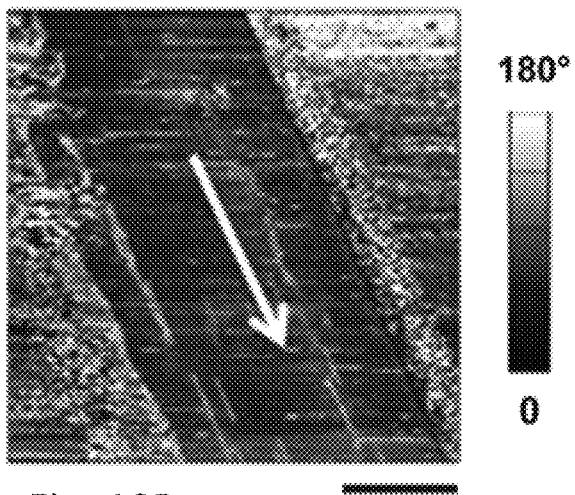
Figure 10E:
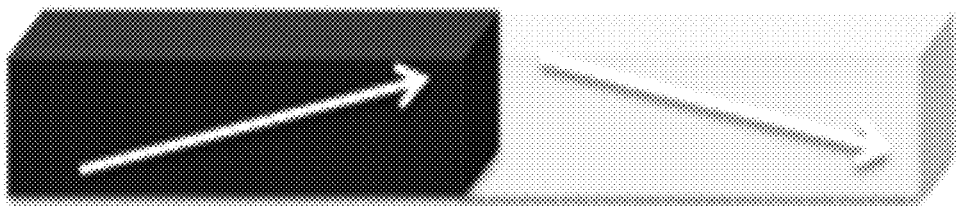
Figure 10F:
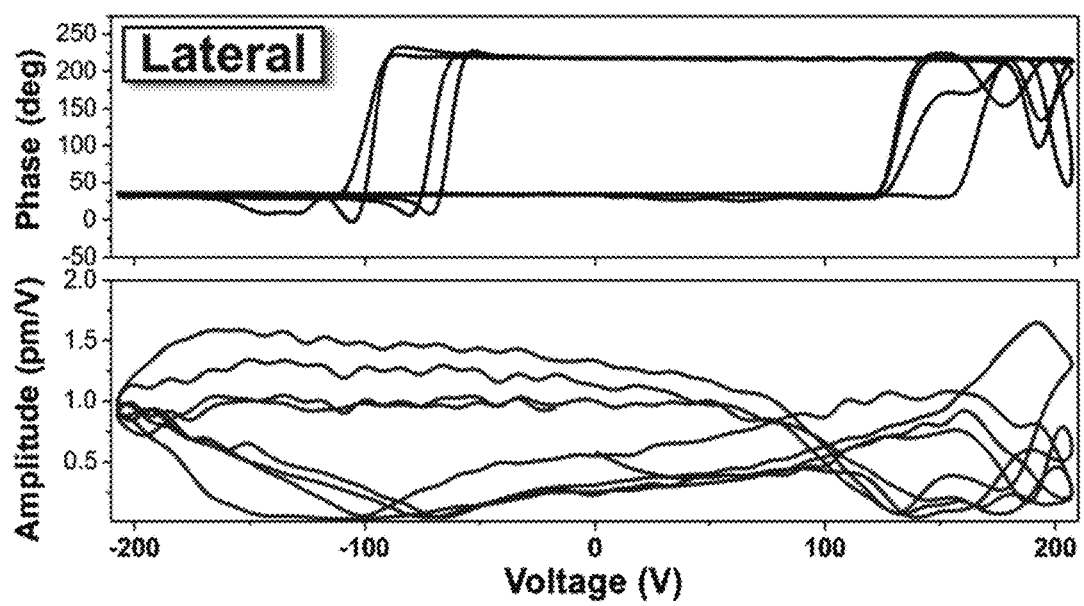
Figure 10G:
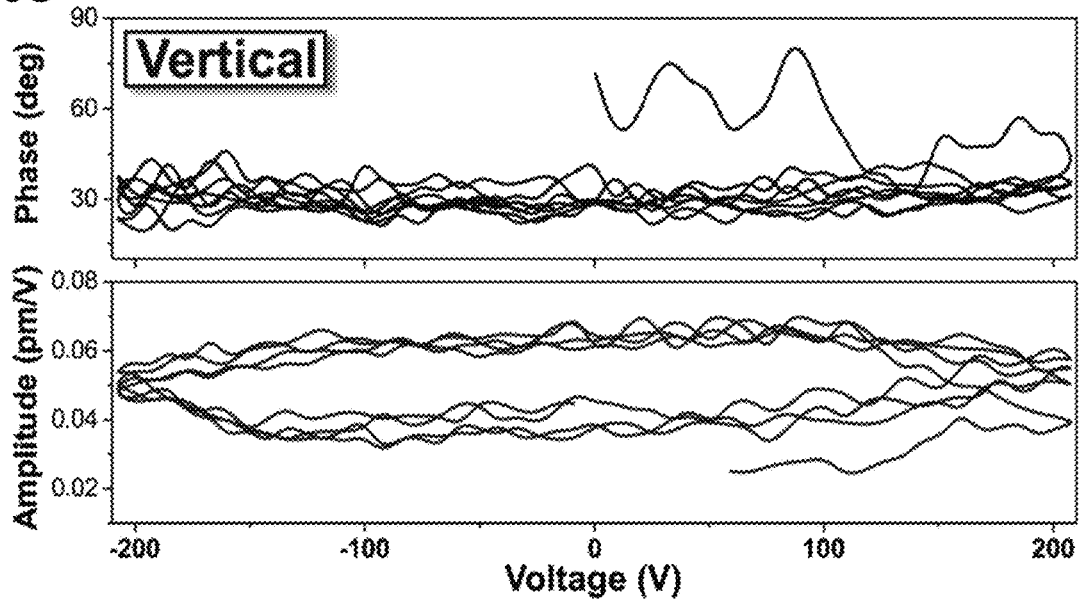
Figure 10H:
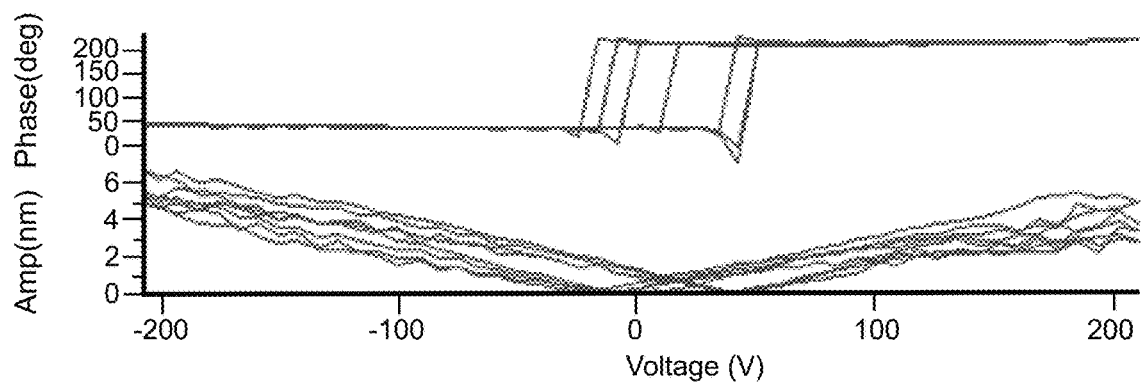
Figure 10I:
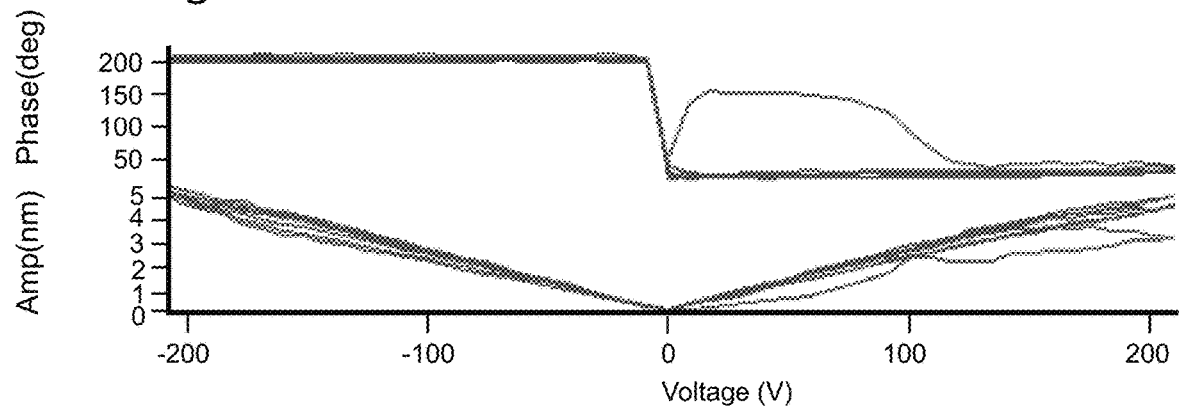

Interestingly, this situation changed when the crystals with the crystallographic a-axis perpendicular to the widest face were probed. (See, FIGS. 10A-10G.) For mixed crystals of 2·7, we were able to switch the lateral piezoresponse by applying vertical field, which implies polarization switching by external electric field. This strongly suggests that sample 2·7 possess ferroelectric properties along the polar axis (c-axis) of the crystal. FIGS. 10F-10I show the vertical and lateral piezoresponse hysteresis loops measured using both pulse and continuous modes (or 'on' and 'off' modes), respectively. As shown in FIGS. 10H-10I, the cantilever-sample interaction is strong, even though we used stiff cantilevers with high aspect ratio tip, probably due to the large voltage that was applied in an attempt to switch the polarization. In such cases, hysteresis loops obtained by pulse dc mode provide clearer picture on identifying switchable polarization. FIGS. 10F-10G present such loops and show that only the lateral piezoresponse can be switched from one direction to the other upon external electric field, whereas the vertical piezoresponse cannot be switched within the voltage range of 200 V.

Figure 11A:
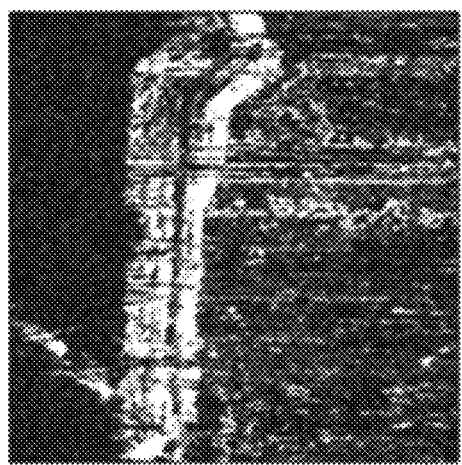
FIGS. 11A-11D show PFM images and piezoresponse hysteresis loops of 8.
Figure 11B:
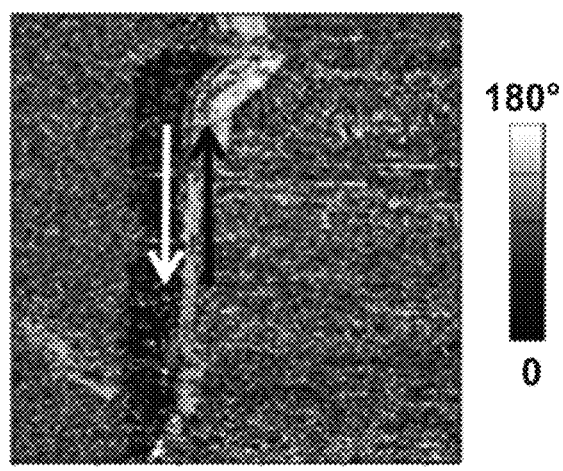
Figure 11C:
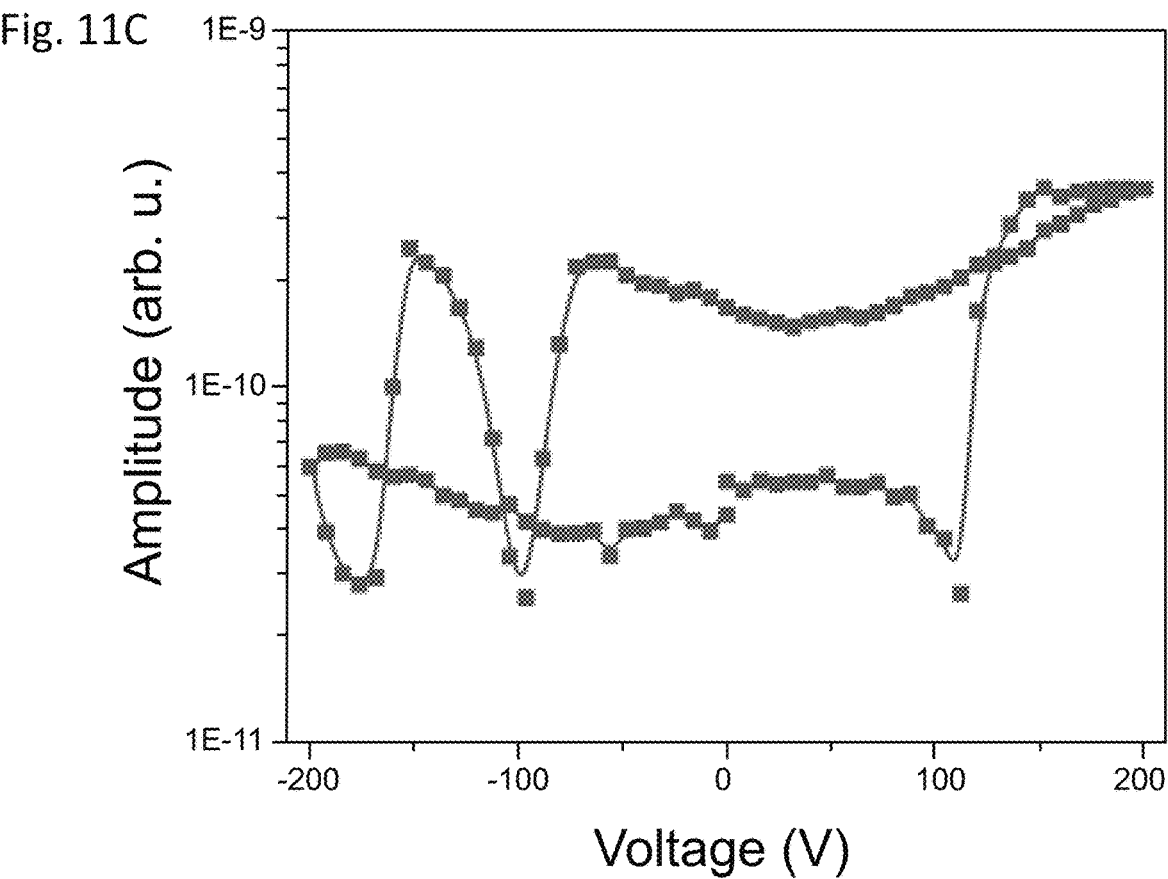
Figure 11D:
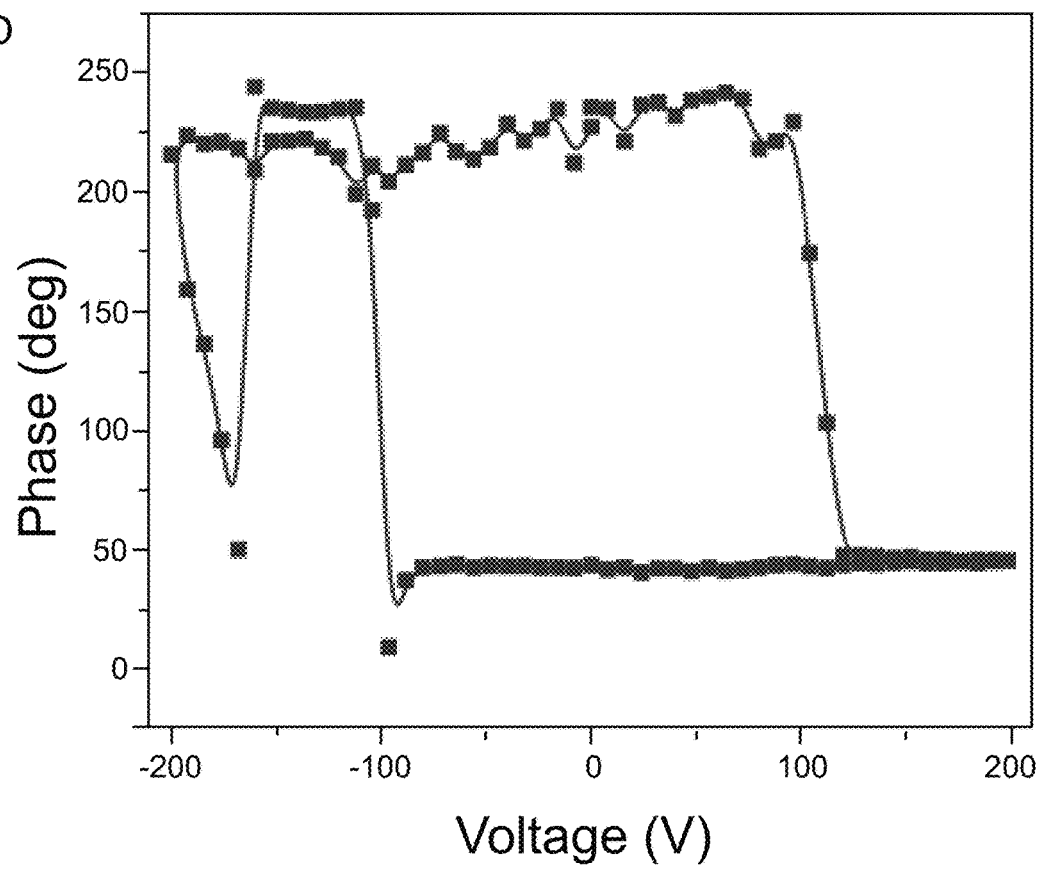

Both vertical and lateral PFM were used to confirm the presence of the ferroelectric and piezoelectric properties in single-component crystals of 8, which axes orientation is the same as of 2·7. The crystals of 8 exhibited even weaker vertical piezoresponse than sample 2·7, indicating more alignment of the polarization along the long axis of the crystal. As shown in FIGS. 11A-11B, the lateral PFM images showed similar in-plane polarization domain structure to sample 2. In addition, the piezoresponse hysteresis loop measurement indicated switchable in-plane polarization (FIGS. 11C-11D) by external electric field in 8 similar to sample 2·7 as well as prototypical polymer ferroelectrics. Although the mobility of molecules about the N—H • • • N hydrogen bonds—that is postulated in this work as an explanation for both the natural distortion of crystals and the observed relaxation processes—might also explain the ease of the lateral piezoresponse switching when an external field is applied along N—H • • • N chains.

In summary, haloimidazoles constitute a rare case of room-temperature ferroelectric materials on account of their non-centrosymmetric crystal lattice with the polar direction orthogonal to the direction of the N—H • • • N chains. The tendency of haloimidazoles to produce naturally distorted crystals has its roots in the imbalance of crystal packing forces, with halogen bonding playing a substantial role. The halogen bond networks in haloimidazoles can be disrupted in a controllable way by the addition of halogenated alkylimidazoles, producing flexible, non-centrosymmetric crystals of organic ferroelectrics.

The unique combination of electrical and mechanical properties, enhanced by the structural simplicity of haloimidazole molecules, clearly demonstrates that organic materials may provide alternative sources of piezoelectrics and ferroelectrics. The attractions of the haloimidazoles are their ease of synthesis, coupled with the ability to make simple structural modifications so as to perturb the hydrogen bond chains and weak halogen networks governing the physical properties of these crystalline systems.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

As used herein, except where the context requires otherwise the term "comprise" and variations of the term, such as "comprising", "comprises" and "comprised", are not intended to exclude other additives, components, integers or steps.

All references, including publications, patent applications, and patents, cited herein are hereby incorporated by reference to the same extent as if each reference were individually and specifically indicated to be incorporated by reference and were set forth in its entirety herein, except to the extent that it is contradictory with the present application. Reference to any prior art in the specification or any application from which priority is claimed is not, and should not be taken as, an acknowledgment or any form of suggestion that this prior art forms part of the common general knowledge in any other jurisdiction or that this prior art could reasonably be expected to be ascertained, understood and regarded as relevant by a person skilled in the art.

EXAMPLES

Materials & General Methods & Instrumentation. 4,5-Dichloro-2-methylimidazole (1) (Alfa Aesar, 97%) and 4,5-dibromo-2-methyl-imidazole (2) (Combi-Blocks, 98%) were used as received. 2,4,5-Trichloroimidazole (4), 2,4,5-tribromoimidazole (5), 2,4-dibromo-5-methylimidazole (8), 4,5-dibromo-2-ethyl-imidazole (10), 2,4,5-triiodoimidazole (11), and 2-bromo-4,5-dimethyl-imidazole (12) were prepared according to literature procedures. [Lutz, A. W. & Delorenzo, S. Novel halogenated imidazoles. Chloroimidazoles. J. Heterocycl. Chem. 4, 399-402, (1967); Bahnous, M., Mouats, C., Fort, Y. & Gros, P. C. Convenient multigram scale synthesis of polybrominated imidazoles building blocks. Tetrahedron Lett. 47, 1949-1951, (2006); Grosse, S. et al. Access to imidazo[1,2-a]imidazolin-2-ones and functionalization through Suzuki-Miyaura cross-coupling reactions. Eur. J. Org. Chem. 2013, 4146-4155, (2013); Gilligan, P. J. & Bakthavatchalam, R. Synthesis of 6-substituted imidazo[4,5-d]pyridazin-7-ones. Heterocycles 60, 1329-1337, (2003); Iddon, B. & Lim, B. L. Metal-halogen exchange reactions of mono- and poly-halogenoimidazoles. J. Chem. Soc., Perkin Trans. 1, 735-739, (1983); and Serpell, C. J., Kilah, N. L., Costa, P. J., Felix, V. & Beer, P. D. Halogen bond anion templated assembly of an imidazolium pseudorotaxane. Angew. Chem. Int. Ed. 49, 5322-5326, (2010).] All starting materials and reagents were purchased from commercial suppliers and used without further purification. Nuclear magnetic resonance (NMR) spectra were recorded at 298 K on Bruker Avance 500 spectrometer, with working frequencies of 500 MHz for $^1$H, and 125 MHz $^{13}$C nuclei. Chemical shifts are reported in ppm relative to the signals corresponding to the residual non-deuterated solvent. All $^{13}$C NMR spectra were recorded with the simultaneous decoupling of proton nuclei. Electrospray ionisation (ESI) mass spectra were obtained on an Agilent 6210 LCTOF high-resolution mass spectrometer. The phase situation of haloimidazoles was investigated using a Perkin Elmer 8500 Differential Scanning Calorimeter (DSC) calibrated with n-heptane and indium. Hermetically sealed Al pans with the polycrystalline material were prepared in a controlled-atmosphere $N_2$ glovebox. DSC curves did not show any phase transitions between 110 K and melting points of the samples. Agilent Technologies 1260 Infinity Quaternary LC System connected to an Agilent Technologies 6120 Single Quadrupole LC/MS System was used for High Performance Liquid Chromatography (HPLC) analyses. Crystals of mixed solutions were dissolved separately in MeCN before subjected to HPLC.

Synthesis and crystallisation. Compounds 1 and 2 were purchased from commercial suppliers, and were used as received. Syntheses of compounds 3-12 were performed according to previously reported procedures, or their adaptations (see Supplementary Methods for more details). Crystals and mixed crystals of haloimidazoles were grown from $Me_2CO/H_2O$ solution by slow evaporation of the more volatile solvent ($Me_2CO$).

4,5-Diiodo-2-methylimidazole (3): Iodination of 2-methylimidazole was performed following the synthetic procedure reported[16] for the preparation of 2-ethyl-4,5-diiodoimidazole. A solution of 2-methylimidazole (1.24 g, 15.1 mmol) in 2M aqueous NaOH (32 mL) was added to a solution of iodine (7.67 g, 30.2 mmol) in $CHCl_3$ (37 mL). The mixture was stirred at room temperature for 26 h. A saturated aqueous $Na_2S_2O_3$ solution (40 mL) was added to the reaction mixture and the $CHCl_3$ layer was discarded. Neutralisation of the aqueous layer to pH 7 by adding AcOH precipitated a crude yellow product which was collected by filtration and washed with $H_2O$ (40 mL). Recrystallization from $H_2O$, after treatment with activated charcoal, gave pure 4,5-diiodo-2-methylimidazole (3) as a white powder (4.42 g, 88%). $^1$H NMR ($CD_3SOCD_3$, 298 K, 500 MHz): δ 12.48 (s, 1H), 2.27 (s, 3H). $^{13}$C NMR ($CD_3SOCD_3$, 298 K, 126 MHz): δ 150.0, 94.4, 76.0, 13.9. FIRMS: (m/z) calcd for [M+H]$^+$: 334.8537; found 334.8535.

2-Bromo-4,5-dichloroimidazole (6): 4,5-Dichloroimidazole was prepared following an established literature procedure[10]. Neat $Br_2$ (2.42 g, 14.6 mmol) was added dropwise with stirring to a mixture of 4,5-dichloroimidazole (2.01 g, 14.6 mmol), $KHCO_3$ (1.46 g, 14.6 mmol) and DMF (10 mL) at 0° C. The reaction mixture was heated to 95 C and stirred at that temperature for 3 h until complete as indicated by TLC ($CH_2Cl_2$/MeOH 10/1, $R_f$=0.46). After cooling, $H_2O$ (100 mL) was added, and the precipitate was collected by filtration, washed with $H_2O$ (30 mL), dissolved in 5% aqueous NaOH and precipitated by adding 10% aqueous HCl. The solid was collected by filtration and washed with copious amounts of $H_2O$ until the filtrate was neutral. Drying afforded 693 mg (22%) of 2-bromo-4,5-dichloroimidazole (6) as a white solid. $^1$H NMR ($CDCl_3$, 298 K, 500 MHz): δ 9.18 (s, 1H). $^{13}$C NMR ($CD_3COCD_3$, 298 K, 126 MHz): δ 128.8, 119.8, 114.1. HRMS: (m/z) calcd for [M+H]$^+$: 216.8749; found 216.8746.

2,4-Dibromo-5-chloroimidazole (7): The synthesis of 2,4-dibromo-5-chloroimidazole was carried out in two steps starting from 4-bromoimidazole. 4-Bromo-5-chloroimidazole was synthesised following the previously reported[10] literature procedure. Neat $Br_2$ (838 mg, 5.2 mmol) was added dropwise with stirring to a mixture of 4-bromo-5-chloroimidazole (930 mg, 5.1 mmol), $KHCO_3$ (518 mg, 5.2 mmol) and DMF (10 mL) at 0° C. The reaction mixture was heated to 95° C. and stirred at that temperature for 3 h until complete as indicated by TLC ($CH_2Cl_2$/MeOH 10/1, $R_f$=0.56). After cooling, $H_2O$ (100 mL) was added, and the precipitate was collected by filtration, washed with $H_2O$ (30 mL), dissolved in 5% aqueous NaOH, and precipitated by adding 10% aqueous HCl. The solid, which was collected by filtration and washed with copious amounts of $H_2O$ until the filtrate was neutral, was dried, yielding 900 mg (67%) of 2,4-dibromo-5-chloroimidazole (7) as a white crystalline powder. $^1$H NMR ($CDCl_3$, 298 K, 500 MHz): δ 9.21 (s, 1H). $^{13}$C NMR ($CD_3COCD_3$, 298 K, 126 MHz): δ 125.7, 115.6, 103.0. HRMS: (m/z) calcd for [M+H]$^+$: 260.8246; found 260.8254.

4,5-Dichloro-2-ethylimidazole (9): 2-Ethylimidazole (1.00 g, 10 mmol) was added to a solution of NaOH (400 mg, 10 mmol) in 16.7 g of 10-15% aqueous NaOCl with stirring. The colour of the solution transitioned from its initial colourless state through yellow to deep orange during a 5 min reaction period. The pH was adjusted to 4 with conc HCl, resulting in the precipitation of a crude orange coloured product. The precipitate was collected by filtration, washed with $H_2O$ and dried. Recrystallization from $H_2O$, after treatment with activated charcoal, gave pure 4,5-dichloro-2-ethylimidazole (9) as a white solid (446 mg, 27%). $^1$H NMR ($CDCl_3$, 298 K, 500 MHz): δ 9.33 (s, 1H), 2.70 (q, J=7.6 Hz, 2H), 1.30 (t, J=7.6 Hz, 3H). $^{13}$C NMR ($CDCl_3$, 298 K, 126 MHz): δ 147.44, 124.95, 109.52, 22.45, 12.15. HRMS: (m/z) calcd for [M+H]$^+$: 164.9981; found 164.9985.

Microscopy. The optical images were acquired using Olympus BX53 upright microscope. Scanning Electron Microscopy (SEM) images were collected on a Hitachi S-3400N-II SEM microscope at Northwestern University's EPIC/NUANCE facility and on a Hitachi S-3400N SEM at the Laboratory of Electron Microscopy at University of Wroclaw (Poland). Accelerating voltage of 4-8 kV, and a secondary or backscattered electrons detector (SE or BSE) were used. Samples were coated with Au/Pd to ~5 nm thickness using a Denton Desk IV Sputter Coater or a Cressington 108A Gold Evaporator before imaging.

Single-crystal X-ray diffraction measurements. X-Ray quality crystals of haloimidazoles 1-10 were grown from H$_2$O/Me$_2$CO solutions by slow evaporation. Single crystals of 11 and 11.MeOH were obtained by slow evaporation of MeCN and MeOH solutions, respectively. Solid solutions were prepared by dissolving the two components in a mixture of H$_2$O and Me$_2$CO in a Petri dish of a diameter 5 cm and evaporating the solvents at room temperature. The amount of materials taken for each solid solution are listed in Table 8. The ratio and the rate of crystallisation were optimized so that elastic needle-shape crystals (~50 µm in width) were obtained. Diffraction measurements were performed on a Bruker Kappa APEX 2 diffractometers (ω and φ scans), equipped with MoKα sealed tube with Triumph monochromator or CuKα microsource, and CCD area detector, or Xcalibur diffractometer with graphite monochromated MoKα radiation and CCD area detector. Using Olex2 (Dey, D., Mohan, T. P., Vishalakshi, B. & Chopra, D. Computational study of the formation of short centrosymmetric N—H • • • S supramolecular synthon and related weak interactions in crystalline 1,2,4-triazoles. *Cryst. Growth Des.* 14, 5881-5896, (2014).), the structure was solved with the ShelXS (Jungk, T., Hoffmann, Á. & Soergel, E. Challenges for the determination of piezoelectric constants with piezoresponse force microscopy. *Appl. Phys. Lett.* 91, 253511, (2007).) structure solution program using direct methods and refined with the ShelXL with anisotropic thermal parameters for non-H atoms. All H atoms were treated as riding and placed in geometrically optimized positions. H atoms of NH groups in 11 were refined with 0.5 site occupancy factors as they could not be located from the molecular geometry and in the difference Fourier map. In the case of mixed crystals, the initial refinements included C4-C5 distance restrain (1.5 Å), but it was removed during the final stages of the refinement. The crystal data, together with experimental and refinement details, are given in Tables 1 and 9. Crystallographic data for the structures have been deposited with the Cambridge Crystallographic Data Centre. These data can be obtained free of charge from the Cambridge Crystallographic Data Centre via www.ccdc.cam.ac.uk/getstructures. Although the crystal structures of 2 and 12 have been already published, the previously reported crystal data of both compounds are shown in Table 1 for the sake of completeness.

Theoretical calculations. Wave function files of crystal structures were generated at B3LYP/6-311++G(d,p) level of theory using the Gaussian 09 program, and AIM analyses were performed with the AIMAll program. In comparison with the actual crystal structure of haloimidazoles where the hydrogen atom is disordered between two sites in the N—H • • • N bridge, the position of the NH hydrogen atom was fixed so that it belongs to only one nitrogen atom of the imidazole molecule. This procedure did not influence significantly the parameters of the bond critical point (BCP) of intermolecular X • • • X interactions.

The values of the electron density, $\rho(r)$, and the Laplacian of the electron density, $\nabla^2\rho(r)$, at the BCP of halogen-halogen interactions (Table 3) between molecules being related by a 2-fold screw axis (m$_1$ and m$_4$, and m$_4$ and m$_3$) are in accordance with the values for other weak intermolecular contacts, e.g., hydrogen and dihydrogen bonds (criteria range: 0.002-0.035 a.u. and 0.024-0.139 a.u. for $\rho(r)$ and $\nabla^2\rho(r)$, respectively). Higher values of $\rho(r)$ for 2 in comparison to 1 indicate that the substitution of chlorine with bromine increases substantially the strength of the halogen-halogen interactions. The introduction of a halogen atom instead of the methyl group in the second position of imidazole does not provide better stabilisation of the structure. Since contacts involving Cl5 and Cl8 atoms are described by approximately two times lower values of $\rho(r)$ and $\nabla^2\rho(r)$, they are not considered chemical bonds. Low values of the dissociation energy of these contacts, DE$^G$, confirm the lack of interaction.

Information about stability of the X • • • X interactions, the presence of which were confirmed by the AIM method, can be found in other parameters, such as ellipticity, $\varepsilon^{AIM}$, and deviation from linearity, d. Both of them exceed the values that characterize stable intermolecular interactions. This fact indicates substantial susceptibility of these bonds to rupture in case of any structural changes. The process of breaking these bonds and regaining their original position after being deformed is believed to make an important contribution towards the mixed crystals of haloimidazoles acquiring elastic properties. In order to prove this hypothesis, AIM analysis of a reference crystal structure in which halogen-halogen interactions are definitely broken/restored on account of strong structural changes was performed. Hexachlorobenzene, whose crystals can be deformed plastically by applying external force, owes its plastic properties to the restorative effect of the Cl • • • Cl interactions which act cohesively to recover the adhesion between the hexachlorobenzene layers. The BCP parameters of Cl • • • Cl contacts in a hexachlorobenzene structural motif containing three molecules are collected in Table 5. Out of seven bond paths that were identified by the AIM method, two were found to be the interactions that stabilize the structure, and five, because of low values $\nabla^2\rho(r)$ and high values of $\varepsilon^{AIM}$, can be easily ruptured. This fact not only explains the ease in which the layers of π-stacked molecules can glide on top of each other to alleviate the strain, but also gives an important clue as to why mixed crystals of haloimidazoles show elastic properties instead of plastic ones.

Analysis of halogen • • • halogen interactions. Two varieties of halogen-halogen contacts are known—Type I and Type II. While Type I interactions are symmetrical, van der Waals in nature, and are attributed to close packing, Type II interactions arise form electrostatic attractions between polarized halogen atoms. Recently, the following geometric criteria for classification of Type I and Type II contacts were suggested—contacts with $0° \leq |\theta_1-\theta_2| \leq 15°$ are Type I; contacts with $30° \leq |\theta_1-\theta_2|$ are Type II; contacts with $15° \leq |\theta_1-\theta_2| \leq 30°$ are quasi-Type I/Type II. Since Type II halogen-halogen contacts involve interactions between the electrophilic region of one halogen atom with the nucleophilic region of the other, these contacts qualify as being true halogen bonds according to the current IUPAC definition. An analysis (Table 4) of the halogen-halogen interactions of eight isostructural haloimidazoles, 1-8, has shown that Type II halogen-halogen interactions (halogen bonds) are present in the crystal structures of haloimidazoles.

Electric properties. The frequency dependence of the complex electric permittivity, $\varepsilon^* = \varepsilon' - i\varepsilon''$, was measured between 90 and 300 K with an Agilent E4980A Precision LCR Meter in the frequency range 200 Hz to 2 MHz. The samples were ground using a mortar and pestle and the powdered materials were pelleted using 150-180 bar pressure. Copper conductive tape was applied onto opposite faces of each pelleted sample to run permittivity experiments. The overall error in electric permittivity measurements was less than 5%. Bruker Dimension ICON Atomic Force Microscope (AFM), equipped with a Nanoscope V controller in PFM Vertical/Lateral Low Frequency Mode with SCM-PIT cantilevers of nominal spring constant 2.8 N·m$^{-1}$, was used for piezoelectric measurements. Imaging was performed in contact mode at a vertical deflection setpoint of 10 nm, a scan rate of 0.1 Hz, and captured at 512×512 lines. Voltage ramps were performed at a rate of 0.01 Hz and sampled at 1024 points. An AC voltage of 10 Vpp was applied in both calibration and imaging steps in order to ensure beyond any doubt reliable comparison between samples. For the piezoresponse force microscopy (PFM) imaging and hysteresis loop measurement, MFP-3D (Asylum Research, Oxford Instrument) was used with PPP-EFM (Nanosensors, 1.7-2.5 N/m). We used dual ac resonance tracking (DART) mode for both vertical and lateral PFM imaging as well as piezoresponse hysteresis loop measurements. The drive voltage was 5 V and drive frequencies were 350 kHz and 655 kHz for vertical and lateral PFM experiments, respectively. Crystals for PFM measurements were grown from MeOH/$H_2O$ or $Me_2CO/H_2O$ solutions on a glass slide coated with Au/Pd layer ~15 nm thick.

Electric permittivity measurements. Electric permittivity is related directly to the polarisation of the system, and therefore to the dipole moment of molecules in a crystal. In the case of the hydrogen-bonded haloimidazoles, two possible mechanisms that may change the value of the dipole moment in either x, y or z crystallographic direction need to be considered: proton transfer in N—H • • • N hydrogen bridges and the tilting of molecules from their original positions when an alternating electric field is applied. While the proton motion is fast and occurs usually in a high frequency region, the libration motion of molecules seem to be a more likely mechanism. The analysis of the closest environment of the molecule in the crystal lattice revealed that each molecule is surrounded by eight halogen atoms that form a cube inside which the molecule is located. While halogen and N—H • • • N bonds stabilize the molecule on one side of the cube, no interactions are present on the other side of the cube, a situation which is reflected by the significantly larger thermal ellipsoid of the carbon atom of the $CH_3$ group. Therefore, the molecular mobility in the crystal lattice is not completely restricted, allowing the $CH_3$ group to perform a precessive motion or the whole molecule to exhibit a swinging motion, which manifests itself as the relaxation processes when an alternating electric field is applied.

Piezoresponse force microscopy. Piezoresponse Force Microscopy (PFM) is a variation of contact Atomic Force Microscopy (AFM) in which a conductive nanoscale stylus is scanned across the surface. At each pixel an AC electric field is applied between the sample and tip, and the corresponding mechanical excitation is detected through the vibration of the cantilever. For a piezoelectric sample, the oscillating electric field induces a linear mechanical strain, which is related through the third order piezoelectric tensor for the material. Thus, we can image the piezoelectric response at a fixed voltage over the sample and image the linear response of the material quantitatively by sweeping the voltage at fixed points, all while correlating with the topography.

The mechanical deflection of the cantilever in response to the electromechanical coupled strain of the material is detected through the use of a lock-in amplifier. The original AC driving signal is used as a reference signal in two lock-in amplifiers, which detect both the vertical deflection of the cantilever and the lateral in-plane torsion. Since the piezoelectric response is a third order tensor, we can have an in-plane response from a vertical field that is forbidden from both the second order electrostrictive response and the electrostatic response. The magnitude and the phase of the mechanical oscillation are recorded point-by-point, and together yield quantitative information about the orientation of the piezoelectric response of the material.

In order to ensure the instrument is operating properly, we first of all image a periodically poled lithium niobate (PPLN) crystal in which ferroelectric domains of opposite orientation have been written electrically into the sample. Between these domains the orientation of the net polarisation flips 180 degrees out of the plane, resulting in a corresponding 180 degree phase shift of the vertical signal which was easily visualized directly before performing the experiments in this work.

As we are often detecting picometer scale vibrations in PFM, the technique is very sensitive to external vibrations in the surrounding environment, a situation which can often dominate the signal. Thus, it is of key importance to, first of all, choose an AC excitation frequency with a low background contribution, and secondly, furthermore, to subtract the remaining signal from images. Following the procedure of Jungk et al. Challenges for the determination of piezoelectric constants with piezoresponse force microscopy. *Appl. Phys. Lett.* 91, 253511, (2007), we first of all performed frequency sweeps of both the vertical and lateral phase and amplitude signals on a grounded glass slide. Five sweeps were captured and averaged for each channel. As glass is both non-piezoelectric and non-ferroelectric, the recorded frequency spectrum should be a pure measurement of the background signal. In reality, although the phase component often oscillates widely in such samples, it still remains an effective way of choosing an operating frequency with limited background contribution and the only simple way of measuring the background contribution of the lateral signal. Therefore, the vertical signal for selected frequencies is compared to the background spectrum from a quantitative calibration method in order to justify the use of the lateral background amplitude when correcting images.

Next, we measured the frequency dependent quadrature and in-phase signals for a +c and −c domain on the previously imaged PPLN crystal. At the centre of the positively and negatively poled regions, sweeps for amplitude and phase were collected and averaged over five samples. When operating far from contact resonance—typically in the hundreds of kHz range—the majority of the peaks in the spectrum, when combined appropriately, arise from spurious background vibrations. All data collected in this research and reported in this article were obtained in the low frequency regime far from the mechanical resonance in order to avoid issues with topographical cross-talk. Thus, the signals from the opposite domains are added and averaged in order to obtain the pure background signal for the vertical signal of the system.

Finally, the magnitude and phase of the background signal were compared (Table 17) between the PPLN sample and the glass slide. Good agreement is found between the measurements for 35.0 kHz. Therefore, images presented in this article were corrected using the background amplitude for the vertical and lateral amplitude images recorded at the same deflection setpoint and $10V_{pp}$. As the phase signal is highly variable for a non-piezoelectric sample and no easy calibration sample exists for the lateral signal, the phase images are presented untouched.

The geometry employed in the experiment was prepared such that the AFM probe engaged vertically on the shortest axis of the crystal, corresponding to the crystal face (010) or (100) for 2 and 7, respectively. From the solid-state structure, obtained by X-ray crystallography, we can determine the orientation of the crystal from the ratio of the physical dimensions of each crystal. The deflection sensitivity of the cantilever was measured by ramping the cantilever against a hard silicon dioxide substrate and measuring the slope of the linear deflection segment. The deflection sensitivity was recorded to be 106 nm V$^{-1}$ which compares well with the nominal value of 110 nm V$^{-1}$ for SCM PIT provided by Bruker. This value is used in the main section of the article to convert mV V$^{-1}$ piezoelectric coefficients to a value in the traditional units of nm V$^{-1}$.

Nanoindentation tests. Mechanical properties of the elastic solid solution crystals were measured at ambient temperature using a Hysitron Triboindenter TI 950 system at Northwestern University's EPIC/NUANCE facility. A Berkovitch diamond indenter tip was used to assess the hardness and elastic moduli of the crystals. A trapezoid load-unload function was used for each indent spot: 10 s linear loading and 10 s unloading segments with a dwelling of 6 s at the peak load. The maximum load was applied to all samples at a depth of 250 nm. The final values of hardness and elastic modulus presented in Table 16 represent an average of five indentations performed in different spots on the same material.

TABLE 1

Crystal data and structure refinement parameters for 1-6.

| | 1 | 2[1] | 3a | 3b | 4[2] | 5[2] | 6 |
|---|---|---|---|---|---|---|---|
| Empirical formula | $C_4H_4Cl_2N_2$ | $C_4H_4Br_2N_2$ | $C_4H_4I_2N_2$ | $C_4H_4I_2N_2$ | $C_3HCl_3N_2$ | $C_3HN_2Br_3$ | $C_3HBrCl_2N_2$ |
| Formula weight/g mol$^{-1}$ | 150.99 | 239.90 | 333.89 | 333.89 | 171.41 | 304.79 | 215.87 |
| Temperature/K | 100 | 150 | 250 | 100 | 100 | 100 | 100 |
| Wavelength/Å | 0.71073 | 0.71073 | 0.71073 | 0.71073 | 1.54178 | 0.71073 | 0.71073 |
| Crystal system | Orthorhombic | Orthorhombic | Orthorhombic | Orthorhombic | Orthorhombic | Orthorhombic | Orthorhombic |
| Space group | Ama2 | Ama2 | Ama2 | Ama2 | Ama2 | Ama2 | Ama2 |
| a/Å | 9.9314(8) | 10.0598(11) | 10.1538(3) | 10.1862(2) | 9.9548(15) | 10.119(2) | 9.9391(8) |
| b/Å | 15.9458(12) | 16.5717(19) | 17.6311(6) | 17.5316(3) | 16.151(3) | 16.618(3) | 16.2112(15) |
| c/Å | 3.7868(3) | 4.0208(4) | 4.4158(2) | 4.3274(1) | 3.7885(7) | 3.9504(9) | 3.8016(3) |
| V/Å$^3$ | 599.69(8) | 670.30 | 790.53 | 772.79 | 609.11(18) | 664.3(2) | 612.53(9) |
| Z | 4 | 4 | 4 | 4 | 4 | 4 | 4 |
| $D_{calc}$/Mg m$^{-3}$ | 1.672 | 2.377 | 2.805 | 2.870 | 1.869 | 3.048 | 2.341 |
| μ/mm$^{-1}$ | 0.96 | 11.99 | 7.87 | 8.05 | 12.70 | 18.11 | 7.46 |
| F(000) | 304 | 448 | 592 | 592 | 336 | 552 | 408 |
| Crystal size/mm$^3$ | 0.35 × 0.07 × 0.04 | 0.58 × 0.06 × 0.04 | 0.48 × 0.11 × 0.01 | 0.37 × 0.25 × 0.13 | 0.47 × 0.06 × 0.01 | 0.85 × 0.12 × 0.03 | 0.15 × 0.05 × 0.02 |
| θ range/° | 3.3-29.6 | 5-27 | 3.1-35.6 | 4.0-36.5 | 7.1-63.6 | 4.0-32.6 | 2.5-30.1 |
| Ranges of h, k, l | −13 ≤ h ≤ 13, −22 ≤ k ≤ 22, −5 ≤ l ≤ 5 | −12 ≤ h ≤ 13, −21 ≤ k ≤ 21, −5 ≤ l ≤ 5 | −14 ≤ h ≤ 16, −28 ≤ k ≤ 28, −7 ≤ l ≤ 7 | −16 ≤ h ≤ 17, −29 ≤ k ≤ 28, −7 ≤ l ≤ 7 | −11 ≤ h ≤ 11, −18 ≤ k ≤ 17, −4 ≤ l ≤ 4 | −15 ≤ h ≤ 15, −24 ≤ k ≤ 24, −5 ≤ l ≤ 5 | −14 ≤ h ≤ 14, −20 ≤ k ≤ 22, −5 ≤ l ≤ 4 |
| Absorption correction | multi-scan | multi-scan | multi-scan | numerical | multi-scan | numerical | multi-scan |
| Reflections collected/unique | 7476/887 | 4654/456 | 16859/1890 | 6531/1711 | 1150/434 | 5258/1138 | 3799/878 |
| $R_{int}$ | 0.065 | 0.129 | 0.081 | 0.044 | 0.047 | 0.074 | 0.073 |
| Refinement method | Full-matrix least-squares on F$^2$ | | | | | | |
| Data/restraints/parameters | 887/1/41 | 456/3/41 | 1890/1/41 | 1711/1/42 | 434/1/40 | 1138/1/40 | 878/1/40 |
| Goodness-of-fit on F$^2$ | 1.13 | 1.25 | 1.05 | 1.14 | 1.13 | 1.04 | 1.13 |
| Final R indices [I > 2σ(I)] | $R_1 = 0.0206$, $wR_2 = 0.0507$ | $R_1 = 0.0511$, $wR_2 = 0.1253$ | $R_1 = 0.0315$, $wR_2 = 0.0791$ | $R_1 = 0.0261$, $wR_2 = 0.00724$ | $R_1 = 0.0494$, $wR_2 = 0.1405$ | $R_1 = 0.0363$, $wR_2 = 0.0853$ | $R_1 = 0.0591$, $wR_2 = 0.1474$ |
| R indices (all data) | $R_1 = 0.0218$, $wR_2 = 0.0513$ | $R_1 = 0.0536$, $wR_2 = 0.1286$ | $R_1 = 0.0412$, $wR_2 = 0.0846$ | $R_1 = 0.0269$, $wR_2 = 0.0729$ | $R_1 = 0.0505$, $wR_2 = 0.1413$ | $R_1 = 0.0412$, $wR_2 = 0.0878$ | $R_1 = 0.0639$, $wR_2 = 0.1512$ |
| $Δρ_{max}/Δρ_{min}$/e Å$^{-3}$ | 0.28/−0.23 | 1.07/−1.16 | 0.75/−0.88 | 1.06/−1.46 | 0.87/−0.64 | 1.17/−1.55 | 1.48/−2.14 |
| Flack parameter | 0.08(5) | — | 0.06(4) | 0.11(7) | 0.09(6) | −0.06(5) | 0.02(3) |
| CCDC number | 1425312 | 1030313 | 1425317 | 1425318 | 1425319 | 1425320 | 1425321 |

Crystal data and structure refinement parameters for 1-12.

| | 7 | 8 | 9 | 10 | 11[2] | 11• MeOH | 12[1] |
|---|---|---|---|---|---|---|---|
| Empirical formula | $C_3HN_2ClBr_2$ | $C_4H_4N_2Br_2$ | $C_5H_6N_2Cl_2$ | $C_5H_6N_2Br_2$ | $C_3HI_3N_2$ | $C_6H_2I_6N_4$•(CH$_4$O) | $C_5H_7BrN_2$ |
| Formula weight/g mol$^{-1}$ | 260.33 | 239.91 | 165.02 | 253.94 | 445.76 | 923.56 | 175.03 |
| Temperature/K | 100 | 100 | 100 | 100 | 100 | 250 | 150 |
| Wavelength/Å | 1.54178 | 0.71073 | 0.71073 | 0.71073 | 1.54178 | 1.54178 | 0.71073 |
| Crystal system | Orthorhombic | Orthorhombic | Orthorhombic | Orthorhombic | Monoclinic | Monoclinic | Orthorhombic |
| Space group | Ama2 | Ama2 | Pbca | Pbca | P2$_1$/c | P2$_1$/c | Pbcm |
| a/Å | 10.0186(7) | 10.0665(5) | 9.9749(7) | 10.1725(4) | 13.9023(10) | 11.4563(3) | 3.9495(2) |
| b/Å | 16.4996(8) | 16.6713(9) | 8.6094(8) | 8.7364(4) | 22.1713(15) | 9.1817(2) | 15.8764(7) |
| c/Å | 3.8923(2) | 3.8891(2) | 16.1480(13) | 16.7335(7) | 9.1820(7) | 17.9844(5) | 10.1544(4) |
| β/° | — | — | — | — | 107.162(2) | 94.6221(12) | — |
| V/Å$^{-3}$ | 643.41(6) | 652.68(6) | 1386.8(2) | 1487.12(11) | 2704.2(3) | 1885.60(8) | 636.72(5) |
| Z | 4 | 4 | 8 | 8 | 12 | 4 | 4 |
| $D_{calc}$/Mg m$^{-3}$ | 2.687 | 2.442 | 1.581 | 2.268 | 3.285 | 3.253 | 1.826 |
| μ mm$^{-1}$ | 18.934 | 12.31 | 0.84 | 10.81 | 81.08 | 77.61 | 6.35 |
| F(000) | 480 | 448 | 672 | 960 | 2304 | 1608 | 344 |
| Crystal size/mm$^3$ | 0.12 × 0.02 × 0.01 | 0.31 × 0.04 × 0.02 | 0.35 × 0.35 × 0.04 | 0.42 × 0.13 × 0.01 | 0.36 × 0.11 × 0.02 | 0.49 × 0.08 × 0.05 | 0.14 × 0.12 × 0.02 |

TABLE 1-continued

| θ range/° | 5.4-64.9 | 4.1-29.5 | 3.4-26.4 | 2.4-29.1 | 3.9-66.6 | 6.2-67.6 | 5-27 |
|---|---|---|---|---|---|---|---|
| Ranges of h, k, l | $-10 \leq h \leq 11$ | $-13 \leq h \leq 13$ | $-12 \leq h \leq 12$ | $-13 \leq h \leq 13$ | $-13 \leq h \leq 16$ | $-8 \leq h \leq 13$ | $-5 \leq h \leq 5$ |
|  | $-18 \leq k \leq 18$ | $-22 \leq k \leq 22$ | $-10 \leq k \leq 9$ | $-11 \leq k \leq 13$ | $-26 \leq k \leq 26$ | $-10 \leq k \leq 10$ | $-20 \leq k \leq 20$ |
|  | $-4 \leq l \leq 4$ | $-4 \leq l \leq 5$ | $-20 \leq l \leq 20$ | $-22 \leq l \leq 22$ | $-10 \leq l \leq 10$ | $-20 \leq l \leq 21$ | $-12 \leq l \leq 13$ |
| Absorption correction | multi-scan | multi-scan | multi-scan | multi-scan | multi-scan | integration | multi-scan |
| Reflections collected/unique | 3880/584 | 9442/887 | 12960/1352 | 37909/1981 | 37209/4740 | 14684/3351 | 1300/745 |
| $R_{int}$ | 0.048 | 0.030 | 0.037 | 0.062 | 0.075 | 0.054 | 0.020 |
| Refinement method | | | | Full-matrix least-squares on $F^2$ | | | |
| Data/restraints/parameters | 584/1/43 | 887/1/45 | 1352/0/83 | 1981/0/83 | 4740/0/211 | 3351/0/167 | 745/0/40 |
| Goodness-of-fit on $F^2$ | 1.094 | 1.04 | 1.11 | 1.12 | 1.06 | 1.11 | 0.86 |
| Final R indices [I > 2σ(I)] | $R_1 = 0.0224$ | $R_1 = 0.0143$ | $R_1 = 0.0367$ | $R_1 = 0.0316$ | $R_1 = 0.0726$ | $R_1 = 0.0641$ | $R_1 = 0.0382$ |
|  | $wR_2 = 0.0496$ | $wR_2 = 0.0311$ | $wR_2 = 0.0915$ | $wR_2 = 0.0683$ | $wR_2 = 0.1961$ | $wR_2 = 0.1622$ | $wR_2 = 0.0985$ |
| R indices (all data) | $R_1 = 0.0238$ | $R_1 = 0.0155$ | $R_1 = 0.0412$ | $R_1 = 0.0475$ | $R_1 = 0.0763$ | $R_1 = 0.0654$ | $R_1 = 0.0518$ |
|  | $wR_2 = 0.0500$ | $wR_2 = 0.0314$ | $wR_2 = 0.0955$ | $wR_2 = 0.0760$ | $wR_2 = 0.2052$ | $wR_2 = 0.1641$ | $wR_2 = 0.1046$ |
| $\Delta\rho_{max}/\Delta_{min}$/e Å$^{-3}$ | 0.31/-0.49 | 0.51/-0.28 | 0.41/-0.28 | 0.62/-0.78 | 3.21/-2.52 | 1.86/-3.12 | 0.48/-0.50 |
| Flack parameter | -0.05(6) | 0.02(2) | — | — | — | — | — |
| CCDC number | 1425322 | 1425323 | 1425324 | 1425325 | 1425326 | 1425327 | 960285 |

TABLE 2

Centrosymmetric and noncentrosymmetric point groups in crystals.

| | | Noncentrosymmetric | | |
|---|---|---|---|---|
| Class | Centrosymmetric | | Polar | Nonpolar |
| Cubic | m3 | m3m | None | 432  $\bar{4}$3m  23 |
| Tetragonal | 4/m | 4/mmm | 4  4mm | $\bar{4}$  $\bar{4}$2m  422 |
| Orthorombic | | mmm | mm2 | 222 |
| Hexagonal | 6/m | 6/mmm | 6  mm | $\bar{6}$  $\bar{6}$2m  622 |
| Trigonal | $\bar{3}$ | $\bar{3}$m | 3  3m | 32 |
| Monoclinic | | 2/m | 2  m | None |
| Triclinic | | $\bar{1}$ | 1 | None |
| Number | | 11 group | 10 groups | 11 Groups |

TABLE 4

Halogen-halogen interactions analysis. Geometric parameters, $\theta_1$ and $\theta_1$ angles, of halogen-halogen interactions of 1-8 haloimidazoles and their classification.

| Compound | X...X | $\theta_1$/° | $\theta_2$/° | $|\theta_1 - \theta_2|$ | X...X interaction |
|---|---|---|---|---|---|
| 1 | Cl...Cl | 162.13 | 127.29 | 34.84 | Type II |
| 2 | Br...Br | 162.51 | 122.75 | 39.76 | Type II |
| 3 | I...I | 159.44 | 120.16 | 39.28 | Type II |
| 4 | Cl...Cl | 162.24 | 126.44 | 35.80 | Type II |
| 5 | Br...Br | 161.55 | 125.36 | 36.19 | Type II |
| 6 | Cl...Cl | 162.12 | 127.53 | 34.59 | Type II |

TABLE 3

The characteristic of the bond critical point (BCP) of the intermolecular halogen-halogen contacts of selected haloimidazoles.

| Compound | Atoms | ρ(r) | $\nabla^2$ ρ(r) | G(r) | V(r) | DE$^G$ | ε$^{AIM}$ | d | Bond? |
|---|---|---|---|---|---|---|---|---|---|
| 1 | Cl2...Cl3 | 0.0069 | 0.0282 | 0.0054 | -0.0038 | 0.00232 | 0.1152 | 0.0205 | √ |
| 1 | Cl1...Cl4 | 0.0069 | 0.0279 | 0.0054 | -0.0038 | 0.00232 | 0.1184 | 0.0212 | √ |
| 2 | Br2...Br3 | 0.0079 | 0.0267 | 0.0053 | -0.0039 | 0.00227 | 0.1180 | 0.0138 | √ |
| 2 | Br1...Br4 | 0.0079 | 0.0270 | 0.0054 | -0.0040 | 0.00232 | 0.1155 | 0.0129 | √ |
| 4 | Cl2...Cl3 | 0.0065 | 0.0268 | 0.0051 | -0.0035 | 0.00219 | 0.1167 | 0.0208 | √ |
| 4 | Cl1...Cl4 | 0.0066 | 0.0269 | 0.0051 | -0.0036 | 0.00219 | 0.1176 | 0.0220 | √ |
| 4 | Cl1...Cl5 | 0.0038 | 0.0137 | 0.0025 | -0.0016 | 0.00107 | 0.1325 | 0.0240 | × |
| 4 | Cl2...Cl5 | 0.0038 | 0.0137 | 0.0025 | -0.0016 | 0.00107 | 0.1354 | 0.0251 | × |
| 4 | Cl3...Cl5 | 0.0036 | 0.0114 | 0.0021 | -0.0014 | 0.00090 | 0.0590 | 0.0021 | × |
| 4 | Cl4...Cl5 | 0.0036 | 0.0114 | 0.0021 | -0.0014 | 0.00090 | 0.0525 | 0.0016 | × |
| 4 | Cl7...Cl8 | 0.0036 | 0.0113 | 0.0021 | -0.0013 | 0.00090 | 0.0397 | 0.0016 | × |
| 4 | Cl6...Cl8 | 0.0037 | 0.0113 | 0.0021 | -0.0013 | 0.00090 | 0.0480 | 0.0020 | × |

Symbols:

ρ(r), the electron density;

$\nabla^2$ ρ(r), the Laplacian of the electron density;

G(r), the electron kinetic energy density [a.u.];

V(r), the electron potential energy density [a.u.];

DE$^G$ = 0.429G(r), the dissociation energy [kcal/mol];

ε$^{AIM}$, the ellipticity;

d, the deviation from linearity [Å].

TABLE 4-continued

Halogen-halogen interactions analysis. Geometric parameters, $\theta_1$ and $\theta_1$ angles, of halogen-halogen interactions of 1-8 haloimidazoles and their classification.

| Compound | X...X | $\theta_1/°$ | $\theta_2/°$ | $\|\theta_1 - \theta_2\|$ | X...X interaction |
|---|---|---|---|---|---|
| 7[a] | Br...Br | 160.52 | 125.61 | 34.91 | Type II |
| | Cl...Cl | 167.97 | 126.83 | 41.14 | Type II |
| | Br...Cl | 166.28 | 127.72 | 38.56 | Type II |
| 8 | Br...Br | 163.02 | 128.57 | 34.45 | Type II |

[a] Positional disorder at 4 and 5 positions.

TABLE 5

Bond critical points of hexachlorobenzene. The characteristic of BCP of the intermolecular contacts of hexachlorobenzene.

| Atoms | $\rho(r)$ | $\nabla^2 \rho(r)$ | $G(r)$ | $V(r)$ | $DE^G$ | $\varepsilon^{AIM}$ | d | Stability? |
|---|---|---|---|---|---|---|---|---|
| Cl12...Cl25 | 0.0034 | 0.0111 | 0.0021 | −0.0014 | 0.00090 | 0.3920 | 0.0202 | × |
| Cl7...Cl13 | 0.0059 | 0.0245 | 0.0046 | −0.0032 | 0.00197 | 0.0556 | 0.0163 | √ |
| Cl24...Cl25 | 0.0063 | 0.0261 | 0.0050 | −0.0034 | 0.00215 | 0.0977 | 0.0094 | √ |
| Cl7...Cl24 | 0.0054 | 0.0199 | 0.0037 | −0.0025 | 0.00159 | 0.1068 | 0.0161 | × |
| Cl23...Cl25 | 0.0038 | 0.0133 | 0.0025 | −0.0016 | 0.00107 | 0.1510 | 0.0162 | × |
| Cl12...Cl32 | 0.0057 | 0.0195 | 0.0037 | −0.0025 | 0.00159 | 0.2021 | 0.0008 | × |
| Cl11...Cl32 | 0.0034 | 0.0111 | 0.0021 | −0.0014 | 0.00090 | 0.3939 | 0.0197 | × |

TABLE 6

Parameters of the Cole-Cole relation for selected temperatures for 1 and 3.

| 1 | | | | | 3 | | | | |
|---|---|---|---|---|---|---|---|---|---|
| T (K) | $\tau \times 10^7$ (s) | $\varepsilon_0$ | $\varepsilon_\infty$ | $\alpha$ | T (K) | $\tau \times 10^7$ (s) | $\varepsilon_0$ | $\varepsilon_\infty$ | $\alpha$ |
| 270 | 4.80 | 1.623 | 1.180 | 0.697 | 140 | 37.0 | 3.142 | 2.782 | 0.665 |
| 275 | 3.99 | 1.630 | 1.190 | 0.674 | 155 | 13.0 | 3.153 | 2.782 | 0.626 |
| 280 | 3.15 | 1.626 | 1.199 | 0.646 | 170 | 6.29 | 3.164 | 2.794 | 0.577 |
| 285 | 2.59 | 1.628 | 1.198 | 0.635 | 185 | 3.23 | 3.157 | 2.810 | 0.505 |
| 290 | 2.19 | 1.624 | 1.201 | 0.622 | 200 | 2.00 | 3.160 | 2.819 | 0.444 |

TABLE 7

Parameters of the Havriliak-Negami relation for selected temperatures for 2.

| 2 | | | | | | 2 | | | | | |
|---|---|---|---|---|---|---|---|---|---|---|---|
| T (K) | $\tau \times 10^4$ (s) | $\varepsilon_0$ | $\varepsilon_\infty$ | $\alpha$ | $\beta$ | T (K) | $\tau \times 10^4$ (s) | $\varepsilon_0$ | $\varepsilon_\infty$ | $\alpha$ | $\beta$ |
| 265 | 28.0 | 3.166 | 1.237 | 0.902 | 0.620 | 272 | 2.60 | 3.450 | 1.149 | 0.570 | 0.789 |
| 267 | 18.3 | 3.257 | 1.241 | 0.852 | 0.629 | 273 | 1.89 | 3.435 | 1.146 | 0.608 | 0.595 |
| 269 | 12.0 | 3.378 | 1.224 | 0.843 | 0.556 | 274 | 1.16 | 3.428 | 1.155 | 0.567 | 0.606 |
| 270 | 8.34 | 3.316 | 1.229 | 0.792 | 0.587 | 275 | 0.83 | 3.442 | 1.097 | 0.526 | 0.598 |
| 271 | 6.00 | 3.450 | 1.182 | 0.712 | 0.578 | 276 | 0.69 | 3.432 | 1.134 | 0.535 | 0.596 |

TABLE 8

Mixed crystals preparation. Amounts of materials taken to prepare haloimidazoles solid solutions.

| Solution | Component 1 (disturber) | Component 2 (basic structure) | Mass/mg | Moles/mmol |
|---|---|---|---|---|
| 1•4 | 1 | 4 | $m^1$ = 7.0 | $n^1$ = 0.046 |
| | | | $m^2$ = 7.9 | $n^2$ = 0.046 |
| 1•5 | 1 | 5 | $m^1$ = 14.6 | $n^1$ = 0.097 |
| | | | $m^2$ = 14.0 | $n^2$ = 0.046 |
| 1•6 | 1 | 6 | $m^1$ = 16.4 | $n^1$ = 0.109 |
| | | | $m^2$ = 10.2 | $n^2$ = 0.047 |
| 1•7 | 1 | 7 | $m^1$ = 12.2 | $n^1$ = 0.081 |
| | | | $m^2$ = 10.5 | $n^2$ = 0.040 |
| 2•4 | 2 | 4 | $m^1$ = 10.2 | $n^1$ = 0.043 |
| | | | $m^2$ = 7.10 | $n^2$ = 0.041 |
| 2•5 | 2 | 5 | $m^1$ = 10.4 | $n^1$ = 0.043 |
| | | | $m^2$ = 12.9 | $n^2$ = 0.042 |
| 2•6 | 2 | 6 | $m^1$ = 10.5 | $n^1$ = 0.044 |
| | | | $m^2$ = 4.70 | $n^2$ = 0.022 |
| 2•7 | 2 | 7 | $m^1$ = 10.1 | $n^1$ = 0.042 |
| | | | $m^2$ = 10.6 | $n^2$ = 0.041 |

Symbols:
$m^1$ and $n^1$ - mass and moles of component 1;
$m^2$ and $n^2$ - mass and moles of component 2.

TABLE 9

Crystal data and structure refinement parameters for 1•4, 1•5, 1•6, 1•7, 2•4, 2•5, 2•6, and 2•7 solid solutions.

| | 1•4 | 1•5 | 1•6 | 1•7 |
|---|---|---|---|---|
| Empirical formula | $C_{3.39}H_{2.16}Cl_{2.61}N_2$ | $C_{3.65}H_{2.97}N_2Cl_{1.35}Br$ | $C_{3.7}H_{3.1}N_2Cl_2Br_{0.3}$ | $C_{3.7}H_{3.11}N_2Cl_{1.73}Br_{0.56}$ |
| Formula weight/g mol$^{-1}$ | 163.50 | 200.55 | 170.62 | 181.88 |
| Temperature/K | 100 | 100 | 100 | 100 |
| Wavelength/Å | 0.71073 | 0.71073 | 0.71073 | 1.54178 |
| Crystal system | Orthorhombic | Orthorhombic | Orthorhombic | Orthorhombic |
| Space group | Ama2 | Ama2 | Ama2 | Ama2 |
| a/Å | 9.9471(8) | 9.971(2) | 9.9274(4) | 9.9503(6) |
| b/Å | 16.0705(11) | 16.255(4) | 16.0510(7) | 16.2127(12) |
| c/Å | 3.7773(3) | 3.8480(8) | 3.7886(2) | 3.8233(3) |
| V/Å$^3$ | 603.82(8) | 623.7(2) | 603.69(5) | 616.78(8) |
| Z | 4 | 4 | 4 | 4 |
| $D_{calc}$/Mg m$^{-3}$ | 1.799 | 2.152 | 1.877 | 1.959 |
| μ (mm$^{-1}$) | 1.226 | 7.006 | 2.958 | 11.748 |
| F(000) | 324 | 386 | 335 | 354 |
| Crystal size/mm$^3$ | 0.70 × 0.08 × 0.04 | 0.50 × 0.04 × 0.04 | 0.41 × 0.11 × 0.08 | 0.10 × 0.03 × 0.02 |
| θ range/° | 3.3-30.5 | 2.5-31.0 | 4.8-35.0 | 5.5-66.2 |
| Ranges of h, k, l | $-14 \leq h \leq 14$<br>$-22 \leq k \leq 22$<br>$-5 \leq l \leq 5$ | $-14 \leq h \leq 14$<br>$-23 \leq k \leq 23$<br>$-5 \leq l \leq 5$ | $-16 \leq h \leq 16$<br>$-25 \leq k \leq 25$<br>$-5 \leq l \leq 6$ | $-11 \leq h \leq 11$<br>$-16 \leq k \leq 18$<br>$-4 \leq l \leq 4$ |
| Absorption correction | multi-scan | multi-scan | numerical | multi-scan |
| Refl. collected/unique | 3837/937 | 5385/1028 | 5787/1283 | 2370/545 |
| $R_{int}$ | 0.01011 | 0.052 | 0.053 | 0.028 |
| Refinement method | | | | |
| Data/restraints/parameters | 937/1/44 | 1028/1/52 | 1283/1/45 | 545/1/48 |
| Goodness-of-fit on F$^2$ | 1.06 | 1.06 | 1.09 | 1.07 |
| Final R indices [I > 2σ(I)] | $R_1 = 0.0405$<br>$wR_2 = 0.0941$ | $R_1 = 0.0284$<br>$wR_2 = 0.0625$ | $R_1 = 0.0300$<br>$wR_2 = 0.0683$ | $R_1 = 0.0234$<br>$wR_2 = 0.0583$ |
| R indices (all data) | $R_1 = 0.0474$<br>$wR_2 = 0.0986$ | $R_1 = 0.0352$<br>$wR_2 = 0.0648$ | $R_1 = 0.0354$<br>$wR_2 = 0.0694$ | $R_1 = 0.0248$<br>$wR_2 = 0.0589$ |
| $\Delta\rho_{max}/\Delta\rho_{min}$/e Å$^{-3}$ | 0.34/-0.41 | 0.43/-0.50 | 0.40/-0.29 | 0.36/-0.23 |
| Flack parameter | -0.7(2) | 0.023(19) | 0.04(2) | -0.05(4) |
| CCDC number | 1425308 | 1425309 | 1425310 | 1425322 |

| | 2•4 | 2•5 | 2•6 | 2•7 |
|---|---|---|---|---|
| Empirical formula | $C_{3.37}H_{2.11}N_2Cl_{1.48}Br_{1.15}$ | $C_{3.51}H_{2.52}N_2Br_{2.49}$ | $C_{3.69}H_{3.08}N_2Cl_{0.73}Br_{1.58}$ | $C_{3.55}H_{2.66}N_2Cl_{0.58}Br_{1.87}$ |
| Formula weight/g mol$^{-1}$ | 214.78 | 271.87 | 227.30 | 243.27 |
| Temperature/K | 100 | 100 | 100 | 100 |
| Wavelength/Å | 0.71073 | 0.71073 | 1.54178 | 0.71073 |
| Crystal system | Orthorhombic | Orthorhombic | Orthorhombic | Orthorhombic |
| Space group | Ama2 | Ama2 | Ama2 | Ama2 |
| a/Å | 9.9970(8) | 10.033(4) | 10.0268(6) | 10.0275(5) |
| b/Å | 16.3862(14) | 16.524(7) | 16.4133(10) | 16.4911(8) |
| c/k | 3.8772(4) | 3.9323(15) | 3.9226(2) | 3.9218(2) |
| V/Å$^3$ | 635.14(10) | 651.9(4) | 645.55(6) | 648.53(6) |
| Z | 4 | 4 | 4 | 4 |
| $D_{calc}$/Mg m$^{-3}$ | 2.246 | 2.770 | 2.339 | 2.492 |
| μ (mm$^{-1}$) | 7.909 | 15.343 | 14.769 | 11.826 |
| F(000) | 407 | 499 | 427.0 | 453 |
| Crystal size/mm$^3$ | 0.51 × 0.04 × 0.03 | 0.60 × 0.08 × 0.04 | 0.60 × 0.05 × 0.02 | 0.47 × 0.07 × 0.02 |
| θ range/° | 4.8-30.6 | 2.5-26.4 | 5.4-64.6 | 4.8-35.4 |
| Ranges of h, k, l | $-14 \leq h \leq 14$<br>$-23 \leq k \leq 22$<br>$-5 \leq l \leq 5$ | $-11 \leq h \leq 12$<br>$-20 \leq k \leq 20$<br>$-4 \leq l \leq 2$ | $-11 \leq h \leq 11$<br>$-17 \leq k \leq 18$<br>$-4 \leq l \leq 4$ | $-16 \leq h \leq 16$<br>$-26 \leq k \leq 26$<br>$-6 \leq l \leq 6$ |
| Absorption correction | numerical | multi-scan | multi-scan | multi-scan |
| Refl. collected/unique | 5077/963 | 2361/517 | 3988/551 | 12492/1540 |
| $R_{int}$ | 0.079 | 0.026 | 0.027 | 0.032 |
| Refinement method | | | | |
| Data/restraints/parameters | 963/1/48 | 517/1/45 | 551/1/49 | 1540/1/49 |
| Goodness-of-fit on F$^2$ | 0.982 | 1.09 | 1.08 | 1.05 |
| Final R indices [I > 2σ(I)] | $R_1 = 0.0321$<br>$wR_2 = 0.0690$ | $R_1 = 0.0197$<br>$wR_2 = 0.0475$ | $R_1 = 0.0139$<br>$wR_2 = 0.0328$ | $R_1 = 0.0192$<br>$wR_2 = 0.0349$ |
| R indices (all data) | $R_1 = 0.0415$<br>$wR_2 = 0.0715$ | $R_1 = 0.0203$<br>$wR_2 = 0.0478$ | $R_1 = 0.0140$<br>$wR_2 = 0.0329$ | $R_1 = 0.0253$<br>$wR_2 = 0.0360$ |
| $\Delta\rho_{max}/\Delta\rho_{min}$/e Å$^{-3}$ | 0.75/-0.83 | 0.50/-0.76 | 0.20/-0.25 | 0.49/-0.40 |
| Flack parameter | 0.03(3) | 0.07(4) | 0.09(5) | 0.012(19) |
| CCDC number | 1425313 | 1425314 | 1425315 | 1425316 |

TABLE 10

Calculated (HPLC) and experimental (X-ray) components ratio of 1•5 crystals.[a]
1•5 mixed in 2:1 ratio

| | Crystal 1 | | Crystal 2 | | Crystal 3 | | Crystal 4 | | Crystal 5 | | average | | X-ray | |
|---|---|---|---|---|---|---|---|---|---|---|---|---|---|---|
| Compound | 1 | 5 | 1 | 5 | 1 | 5 | 1 | 5 | 1 | 5 | 1 | 5 | 1 | 5 |
| Peak area [arb.u.] | 389.2 | 280.2 | 197.1 | 137.3 | 509.7 | 376.5 | 396.5 | 284.3 | 322.3 | 226.4 | — | — | — | — |
| $c \times 10^3$ [mol dm$^{-3}$] | 0.138 | 0.076 | 0.072 | 0.041 | 0.179 | 0.100 | 0.140 | 0.077 | 0.115 | 0.063 | — | — | — | — |
| Ratio [%] | 64 | 36 | 64 | 36 | 64 | 36 | 64 | 36 | 65 | 35 | 64 ± 1 | 36 ± 1 | 66 | 34 |

[a]Calculated ratio is compared with the ratio for C5/Br5 atoms in the crystal structure.

TABLE 11

Calculated (HPLC) and experimental (X-ray) components ratio of 1•6 crystals.
1•6 mixed in 2:1 ratio

| | Crystal 1 | | Crystal 2 | | Crystal 3 | | Crystal 4 | | Crystal 5 | | average | | X-ray | |
|---|---|---|---|---|---|---|---|---|---|---|---|---|---|---|
| Compound | 1 | 6 | 1 | 6 | 1 | 6 | 1 | 6 | 1 | 6 | 1 | 6 | 1 | 6 |
| Peak area [arb.u.] | 824.2 | 474.7 | 308.4 | 135.5 | 585.9 | 351.8 | 590.4 | 356.5 | 1053.4 | 631.9 | — | — | — | — |
| $c \times 10^3$ [mol dm$^{-3}$] | 0.286 | 0.140 | 0.110 | 0.045 | 0.205 | 0.106 | 0.206 | 0.107 | 0.364 | 0.184 | — | — | — | — |
| Ratio [%] | 67 | 33 | 71 | 29 | 66 | 34 | 66 | 34 | 66 | 34 | 67 ± 1 | 33 ± 1 | 70 | 30 |

TABLE 12

Calculated (HPLC) and experimental (X-ray) components ratio of 1•7 crystals.[a]
1•7 mixed in 2:1 ratio

| | Crystal 1 | | Crystal 2 | | Crystal 3 | | Crystal 4 | | Crystal 5 | | average | | X-ray | |
|---|---|---|---|---|---|---|---|---|---|---|---|---|---|---|
| Compound | 1 | 7 | 1 | 7 | 1 | 7 | 1 | 7 | 1 | 7 | 1 | 7 | 1 | 7 |
| Peak area [arb.u.] | 1320.3 | 836.3 | 761.7 | 462.2 | 460.2 | 307.1 | 536.2 | 349.9 | 513.2 | 333.1 | — | — | — | — |
| $c \times 10^3$ [mol dm$^{-3}$] | 0.455 | 0.199 | 0.264 | 0.115 | 0.162 | 0.080 | 0.188 | 0.089 | 0.180 | 0.085 | — | — | — | — |
| Ratio [%] | 70 | 30 | 70 | 30 | 67 | 33 | 68 | 32 | 68 | 32 | 69 ± 1 | 31 ± 1 | 71 | 29 |

[a]Calculated ratio is compared with the ratio for C5/Br5 atoms in the crystal structure.

TABLE 13

Calculated (HPLC) and experimental (X-ray) components ratio of 2•5 crystals.
2•5 mixed in 1:1 ratio

| | Crystal 1 | | Crystal 2 | | Crystal 3 | | Crystal 4 | | Crystal 5 | | average | | X-ray | |
|---|---|---|---|---|---|---|---|---|---|---|---|---|---|---|
| Compound | 2 | 5 | 2 | 5 | 2 | 5 | 2 | 5 | 2 | 5 | 2 | 5 | 2 | 5 |
| Peak area [arb.u.] | 457.8 | 534.4 | 253.2 | 290.7 | 918.8 | 1089.6 | 533.6 | 583.8 | 533.8 | 628.8 | — | — | — | — |
| $c \times 10^3$ [mol dm$^{-3}$] | 0.150 | 0.140 | 0.083 | 0.079 | 0.303 | 0.278 | 0.170 | 0.152 | 0.175 | 0.163 | — | — | — | — |
| Ratio [%] | 52 | 48 | 51 | 49 | 52 | 48 | 53 | 47 | 52 | 48 | 52 ± 1 | 48 ± 1 | 51 | 49 |

TABLE 14

Calculated (HPLC) and experimental (X-ray) components ratio of 2•6 crystals.[a]
2•6 mixed in 2:1 ratio

| | Crystal 1 | | Crystal 2 | | Crystal 3 | | Crystal 4 | | Crystal 5 | | average | | X-ray | |
|---|---|---|---|---|---|---|---|---|---|---|---|---|---|---|
| Compound | 2 | 6 | 2 | 6 | 2 | 6 | 2 | 6 | 2 | 6 | 2 | 6 | 2 | 6 |
| Peak area [arb.u.] | 495.3 | 239.5 | 624.3 | 355.1 | 248.0 | 131.2 | 370.2 | 172.7 | 375.9 | 182.8 | — | — | — | — |
| $c \times 10^3$ [mol dm$^{-3}$] | 0.163 | 0.074 | 0.205 | 0.107 | 0.081 | 0.044 | 0.121 | 0.056 | 0.123 | 0.058 | — | — | — | — |
| Ratio [%] | 69 | 31 | 66 | 34 | 65 | 35 | 69 | 31 | 68 | 32 | 67 ± 1 | 33 ± 1 | 69 | 31 |

[a]Calculated ratio is compared with the ratio for C5/Br5 atoms in the crystal structure.

TABLE 15

Calculated (HPLC) and experimental (X-ray) components ratio of 2•7 crystals.[a]
2•7 mixed in 1:1 ratio

| | Crystal 1 | | Crystal 2 | | Crystal 3 | | Crystal 4 | | Crystal 5 | | average | | X-ray | |
|---|---|---|---|---|---|---|---|---|---|---|---|---|---|---|
| Compound | 2 | 7 | 2 | 7 | 2 | 7 | 2 | 7 | 2 | 7 | 2 | 7 | 2 | 7 |
| Peak area [arb.u.] | 959.0 | 984.4 | 539.2 | 604.7 | 294.7 | 315.8 | 691.9 | 746.0 | 803.1 | 895.4 | — | — | — | — |
| $c \times 10^3$ [mol dm$^{-3}$] | 0.316 | 0.233 | 0.177 | 0.147 | 0.096 | 0.082 | 0.228 | 0.179 | 0.265 | 0.213 | — | — | — | — |
| Ratio [%] | 58 | 42 | 55 | 45 | 54 | 46 | 56 | 44 | 55 | 45 | 56 ± 1 | 44 ± 1 | 55 | 45 |

[a]Calculated ratio is compared with the ratio for C5/Br5 atoms in the crystal structure.

TABLE 16

Elastic modulus (E) and hardness (H) of 1•4, 1•5, 1•6, 1•7, 2•4, 2•5, 2•6, and 2•7 solid solution crystals.

| Solid soln | Parameters | Test 1 | Test 2 | Test 3 | Test 4 | Test 5 | average |
|---|---|---|---|---|---|---|---|
| 1•4 | E [GPa] | 0.27 | 0.39 | 0.32 | 0.32 | 0.25 | 0.31 ± 0.02 |
| | H [MPa] | 76.3 | 66.6 | 84.9 | 90.8 | 71.2 | 77.9 ± 4.4 |
| 1•5 | E [GPa] | 0.38 | 0.20 | 0.37 | 0.21 | 0.20 | 0.27 ± 0.04 |
| | H [MPa] | 89.0 | 60.1 | 82.9 | 51.3 | 53.3 | 67.3 ± 7.8 |
| 1•6 | E [GPa] | 0.26 | 0.18 | 0.17 | 0.17 | 0.15 | 0.19 ± 0.02 |
| | H [MPa] | 69.7 | 63.9 | 60.2 | 57.4 | 54.4 | 61.1 ± 2.7 |
| 1•7 | E [GPa] | 0.29 | 0.29 | 0.27 | 0.24 | 0.22 | 0.26 ± 0.01 |
| | H [MPa] | 63.5 | 52.9 | 66.7 | 62.1 | 76.4 | 64.3 ± 3.8 |
| 2•4 | E [GPa] | 0.10 | 0.11 | 0.09 | 0.09 | 0.09 | 0.10 ± 0.05 |
| | H [MPa] | 29.2 | 34.7 | 29.7 | 75.3 | 24.9 | 38.7 ± 9.2 |
| 2•5 | E [GPa] | 0.17 | 0.27 | 0.22 | 0.16 | 0.16 | 0.20 ± 0.05 |
| | H [MPa] | 55.0 | 68.8 | 53.2 | 51.8 | 56.9 | 57.1 ± 3.0 |
| 2•6 | E [GPa] | 0.24 | 0.19 | 0.20 | 0.23 | 0.24 | 0.22 ± 0.01 |
| | H [MPa] | 73.5 | 48.3 | 54.9 | 46.7 | 59.0 | 56.5 ± 4.8 |
| 2•7 | E [GPa] | 0.17 | 0.29 | 0.21 | 0.16 | 0.21 | 0.21 ± 0.02 |
| | H [MPa] | 46.1 | 59.8 | 53.9 | 60.7 | 52.5 | 54.4 ± 2.7 |

TABLE 17

PFM experiments preparation. Comparison of calculated background vectors from both the glass slide and the PPLN samples. Since vertical amplitudes compare well between the methods for 35 kHz, these values of background amplitude were utilized in the correction of vertical and lateral images in the main section.

| f (kHz) | PPLN Vert. Amp. | PPLN Vert. Phase | Glass Vert. Amp. | Glass Vert. Phase | Glass Lat. Amp. | Glass Lat. Phase |
|---|---|---|---|---|---|---|
| 12.5 | 0.1606 mV | −81.2538° | 0.0846 mV | −24.5028° | 0.1343 mV | −7.8750° |
| 35.0 | 0.1678 mV | −56.8581° | 0.1604 mV | −30.0850° | 0.1160 mV | 56.6928° |

What is claimed:

1. A haloimidazole crystal comprising at least two different haloimidazole compounds of formula I:

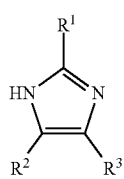

wherein $R^1$, $R^2$, and $R^3$ for the at least two different haloimidazole compounds are independently selected from the group consisting of hydrogen, an alkyl group, and a halogen and at least one of $R^1$, $R^2$, and $R^3$ is a halogen wherein one of the two different haloimidazole compounds is a dihaloimidazole and one of $R^1$, $R^2$, and $R^3$ is an alkyl group, and wherein the crystal has the property of flexiblity.

2. The crystal of claim 1, wherein the dihaloimidazole comprises two different halogens.

3. The crystal of claim 1, wherein the dihaloimidazole comprises two of the same halogen.

4. The crystal of claim 1, wherein the alkyl group is selected from methyl and ethyl.

5. The crystal of claim 1, wherein one of the two different haloimidazole compounds is a trihaloimidazole and wherein the trihaloimidazole comprises at least two different halogens or wherein the trihaloimidazole comprises three of the same halogen.

6. The crystal of claim 1, wherein one of the two different haloimidazole compounds is selected from the group consisting of 4,5-dichloro-2-methylimidazole, 4,5-dibromo-2-methylimidazole, 4,5-diiodo-2-methylimidazole, 2,4,5-trichloroimidazole, 2,4,5-tribromoimidazole, 2-bromo-4,5-dichloroimidazole, 2,4-dibromo-5-chloroimidazole, 2,4-dibromo-5-methylimidazole, 4,5-dichloro-2-ethylimidazole, 4,5-dibromo-2-ethylimidazole, 2,4,5-triiodoimidazole, and 2-bromo-4,5-dimethylimidazole.

7. The crystal of claim 1, wherein the at least two different haloimidazole compounds of formula I comprise the dihaloimidazole and a trihaloimidazole.

8. The crystal of claim 7, wherein the dihaloimidazole is selected from the group consisting 4,5-dichloro-2-methylimidazole, 4,5-dibromo-2-methylimidazole, 4,5-diiodo-2-methylimidazole, 2,4-dibromo-5-methylimidazole, and 4,5-dichloro-2-ethylimidazole, 4,5-dibromo-2-ethylimidazole and/or wherein the trihaloimidazole is selected from the group consisting of 2,4,5-trichloroimidazole, 2,4,5-tribromoimidazole, 2-bromo-4,5-dichloroimidazole, 2,4-dibromo-5-chloroimidazole, and 2,4,5-triiodoimidazole.

9. The crystal of claim 7, wherein the molar ratio of the dihaloimidazole to the trihaloimidazole is between 5:1 to 1:5.

10. The crystal of claim 1, wherein the crystal has a property selected from the group consisting of piezoelectricity, pyroelectricity, ferroelectricity, combinations of any two thereof, and a combination of all three thereof.

11. A mixed crystal comprising a first haloimidazole and a second haloimidazole, wherein the first haloimidazole is a compound of formula I:

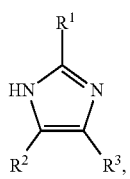

wherein each of $R^1$, $R^2$, and $R^3$ of the first haloimidazole are a halogen,
wherein the second haloimidazole is a compound of formula I:

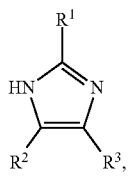

and
wherein $R^1$, $R^2$, and $R^3$ of the second haloimidazole are independently selected from the group consisting of an alkyl group and a halogen and at least two of $R^1$, $R^2$, and $R^3$ are a halogen.

12. The mixed crystal of claim 11, wherein $R^1$ of the second haloimidazole is the alkyl group.

13. The mixed crystal of claim 12, wherein the alkyl group is a methyl group.

14. The mixed crystal of claim 12, wherein both $R^2$ and $R^3$ of the second haloimidazole are the same halogen.

15. The mixed crystal of claim 14, wherein the second haloimidazole is selected from the group consisting of 4,5-dichloro-2-methylimidazole, 4,5-dibromo-2-methylimidazole, and 4,5-diiodo-2-methylimidazole.

16. The mixed crystal of claim 11, wherein each of $R^1$, $R^2$, and $R^3$ of the first haloimidazole are the same halogen.

17. The mixed crystal of claim 16, wherein the first haloimidazole is selected from the group consisting of 2,4,5-trichloroimidazole, 2,4,5-tribromoimidazole, and 2,4,5-triiodoimidazole.

18. The mixed crystal of claim 11, wherein one of $R^1$, $R^2$, and $R^3$ of the first haloimidazole is a different halogen than the other two halogens of the first haloimidazole.

19. The mixed crystal of claim 18, wherein the first haloimidazole is selected from the group consisting of 2-bromo-4,5-dichloroimidazole, 2,4-dibromo-5-chloroimidazole.

20. The mixed crystal of claim 11, wherein the molar ratio of the first haloimidazole to the second haloimidazole is between 5:1 and 1:5.

21. The mixed crystal of claim 11, wherein the crystal has a property selected from the group consisting of piezoelectricity, pyroelectricity, ferroelectricity, flexibility, combinations of any two thereof, combinations of any three thereof, and a combination of all three thereof.

22. A method for preparing a haloimidazole crystal, the method comprising evaporating a solvent from a solution to prepare a crystal having the property of flexibility, the solution comprising the solvent and at least two different haloimidazole compounds of formula I:

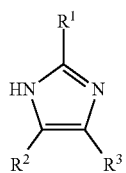

wherein $R^1$, $R^2$, and $R^3$ for the at least two different haloimidazole compounds are independently selected from the group consisting of hydrogen, an alkyl group, and a halogen and at least one of $R^1$, $R^2$, and $R^3$ is halogen and wherein at least one of the two different haloimidazole compounds is a dihaloimidazole and one of $R^1$, $R^2$, and $R^3$ is an alkyl group.

* * * * *